United States Patent [19]

Bernhart et al.

[11] Patent Number: 5,268,375
[45] Date of Patent: Dec. 7, 1993

[54] DINITROGEN HETEROCYCLIC DERIVATIVES N-SUBSTITUTED BY A BIPHENYLMETHYL GROUP, AND THE PHARMACEUTICAL COMPOSITIONS IN WHICH THEY ARE PRESENT

[75] Inventors: Claude Bernhart, Saint Gely Du Fesc; Bernard Ferrari, Les Matelles; Pierre Perreaut, Saint Gely Du Fesc, all of France

[73] Assignee: Elf Sanofi, Paris, France

[21] Appl. No.: 843,239

[22] Filed: Feb. 28, 1992

[30] Foreign Application Priority Data

Mar. 1, 1991 [FR] France .................... 91 02501

[51] Int. Cl.$^5$ .................. C07D 233/36; C07D 239/36; A61K 31/505; A61K 31/415
[52] U.S. Cl. ........................ 514/269; 514/257; 514/387; 514/386; 514/380; 514/383; 514/384; 514/364; 514/363; 544/231; 544/319; 548/300.7; 548/311.1; 548/323.5; 548/324.1; 548/243; 548/263.2; 548/266.2; 548/132; 548/133; 548/138; 548/144
[58] Field of Search ........... 544/231, 298, 319; 514/269, 361, 364, 380, 384, 383, 386, 387, 363, 257; 548/301, 128, 132, 144, 143, 243, 264.2, 266.2, 300.7, 311.1, 243, 132, 144, 323.5, 324.1, 263.2, 266.2, 133, 138

[56] References Cited

U.S. PATENT DOCUMENTS

| | | | |
|---|---|---|---|
| 4,675,403 | 6/1987 | Abou-Gharbia | 548/301 |
| 5,100,897 | 3/1992 | Allen et al. | 514/269 |

FOREIGN PATENT DOCUMENTS

| | | |
|---|---|---|
| 0380959 | 8/1990 | European Pat. Off. ........... 548/301 |
| 0401030 | 12/1990 | European Pat. Off. ........... 548/301 |
| 0407342 | 1/1991 | European Pat. Off. ........... 548/301 |
| 0411766 | 2/1991 | European Pat. Off. ........... 548/301 |
| 0454511 | 10/1991 | European Pat. Off. . |
| 0459136 | 12/1991 | European Pat. Off. . |

Primary Examiner—John M. Ford
Attorney, Agent, or Firm—Bacon & Thomas

[57] ABSTRACT

This invention relates to compounds of formula

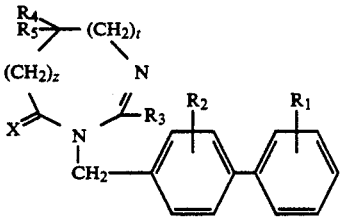

(I)

in which:

$R_1$ and $R_2$ are similar or different and are each independently hydrogen or a group selected from $CO_2N=C(NH_2)_2$, $CONHNHCONH_2$, $CONHNHCSNH_2$, $C(OC_2H_5)=NCO_2CH_3$, $COCH_2CO_2C_2H_5$, $N(OH)$-$CONHCOOC_2NCO_2CH_3$, $COCH_2CO_2C_2H_5$, $N(OH)$-$CONHCOOC_2H_5$, $C(OC_2H_5)=NH$ or a nitrogen heterocycle; with the proviso that at least one of the substituents $R_1$ or $R_2$ is other than hydrogen;

$R_3$ is a hydrogen, a $C_1$-$C_6$ alkyl, a $C_2$-$C_6$ alkenyl, a $C_3$-$C_7$ cycloalkyl, a phenyl, a phenylalkyl, or a phenylalkenyl;

$R_4$ and $R_5$ are each independently a $C_1$-$C_6$ alkyl, a $C_3$-$C_7$ cycloalkyl, a phenyl or a phenylalkyl; or $R_4$ and $R_5$, bonded together, are either a group of the formula $(CH_2)_n$ or a group of the formula $(CH_2)_p$ Y $(CH_2)_q$, in which Y is either an oxygen atom, or a sulfur atom, or a substituted carbon atom, or a group N-$R_6$, in which $R_6$ is a hydrogen, a $C_1$-$C_4$ alkyl, a phenylalkyl, a $C_1$-$C_4$ alkylcarbonyl, a $C_1$-$C_4$ halogenoalkylcarbonyl, a $C_1$-$C_4$ polyhalogenoalkylcarbonyl, a benzolyl, an α-aminoacyl or a N-protecting group, or $R_4$ and $R_5$, together with the carbon atom to which they are bonded, form an indane or an adamantine; $p+q=m$; n is an integer between 2 and 11; m is an integer between 2 and 5; X is an oxygen or a sulfur atom; and z and t are zero or $z+t=1$; and its salts.

5 Claims, No Drawings

DINITROGEN HETEROCYCLIC DERIVATIVES N-SUBSTITUTED BY A BIPHENYLMETHYL GROUP, AND THE PHARMACEUTICAL COMPOSITIONS IN WHICH THEY ARE PRESENT

The present invention relates to N-substituted dinitrogen heterocyclic derivatives, to their preparation and to the pharmaceutical compositions in which they are present.

The compounds according to the invention antagonize the action of angiotensin II, which is a peptide hormone of the formula H-Asp-Arg-Val-Tyr-Ile-His-Pro-Phe-OH.

Angiotensin II is a potent vasopressor and the biologically active product of the renin-angiotensin system: renin acts on the angiotensinogen of the plasma to product angiotensin I, which is converted to angiotensin II by the action of the angiotensin I converting enzyme.

The compounds of the present invention are nonpeptide compounds which antagonize angiotensin II. By inhibiting the action of angiotensin II on its receptors, the compounds according to the invention prevent especially the increase in blood pressure produced by the hormone-receptor interaction; they also have other physiological actions on the central nervous system.

Thus the compounds according to the invention are useful in the treatment of cardiovascular complaints such as hypertension and heart failure, as well as in the treatment of complaints of the central nervous system and in the treatment of glaucoma and diabetic retinopathy.

The present invention relates to compounds of the formula (I)

in which:
  $R_1$ and $R_2$ are similar or different and are each independently hydrogen or a group selected from:
  $CO_2N=C(NH_2)_2$,
  $CONHNHCONH_2$,
  $CONHNHCSNH_2$,
  $C(OC_2H_5)=NCO_2CH_3$,
  $COCH_2CO_2H_5$,
  $N(OH)-CONHCOOC_2H_5$,
  $C(OC_2H_5)=NH$
  or a nitrogen heterocycle selected from:

with the proviso that at least one of the substituents $R_1$ or $R_2$ is other than hydrogen;

$R_3$ is a hydrogen, a $C_1$-$C_6$ alkyl which is unsubstituted or substituted by one or more halogen atoms, a $C_2$-$C_6$ alkenyl, a $C_3$-$C_7$ cycloalkyl, a phenyl, a phenylalkyl in which the alkyl is $C_1$-$C_3$ or a phenylalkenyl in which the alkenyl is $C_2$-$C_3$, said phenyl groups being unsubstituted or monosubstituted or polysubstituted by a halogen atom, a $C_1$-$C_4$ alkyl, a $C_1$-$C_4$ halogenoalkyl, a $C_1$-$C_4$ polyhalogenoalkyl, a hydroxyl or a $C_1$-$C_4$ alkoxy;

$R_4$ and $R_5$ are each independently a $C_1$-$C_6$ alkyl, a $C_3$-$C_7$ cycloalkyl, a phenyl or a phenylalkyl in which the alkyl is $C_1$-$C_3$, said alkyl, phenyl or phenylalkyl groups being unsubstituted or substituted by one or more halogen atoms or by a group selected from a $C_1$-$C_4$ perfluoroalkyl, a hydroxyl and a $C_1$-$C_4$ alkoxy; or $R_4$ and $R_5$, bonded together, are either a group of the formula $(CH_2)_n$ or a group of the formula $(CH_2)_p Y-(CH_2)_q$, in which Y is either an oxygen atom, or a sulfur atom, or a carbon atom substituted by a $C_1$-$C_4$ alkyl group, a phenyl or a phenylalkyl in which the alkyl is $C_1$-$C_3$, or a group N—$R_6$, in which $R_6$ is a hydrogen, a $C_1$-$C_4$ alkyl, a phenylalkyl in which the alkyl is $C_1$-$C_3$, a $C_1$-$C_4$ alkylcarbonyl, a $C_1$-$C_4$ halogenoalkylcarbonyl, a $C_1$-$C_4$ polyhalogenoalkylcarbonyl, a benzoyl, an α-aminoacyl or an N-protecting group, or $R_4$ and $R_5$, together with the carbon atom to which they are bonded, form an indane or an adamantane;

p+q=m;
n is an integer between 2 and 11;
m is an integer between 2 and 5;
X is an oxygen atom or a sulfur atom; and
z and t are simultaneously zero or one is zero and the other is 1;

and their salts.

The compounds of formula I in which $R_1$ is in the ortho position and is a nitrogen heterocycle selected from:

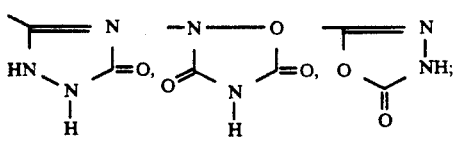

$R_2$ is hydrogen;
$R_3$ is a $C_1$–$C_6$ alkyl;
$R_4$ and $R_5$, together with the carbon to which they are attached, are a group of the formula $(CH_2)_n$;
n is equal to 4 or 5;
z and t are zero or z is 1 and t is zero; and
X is an oxygen atom;
and their salts, are preferred compounds of the invention.

If formed, the salts of the compounds of formula (I) according to the present invention include those with mineral or organic acids which permit a suitable separation or crystallization of the compounds of formula (I), such as trifluoroacetic acid, picric acid, oxalic acid or an optically active acid, for example a mandelic acid or a camphosulfonic acid, and acids which form pharmaceutically acceptable salts such as the hydrochloride, the hydrobromide, the sulfate, the hydrogensulfate, the dihydrogenphosphate, the methanesulfonate, the methylsulfate, the maleate, the fumarate and the naphthalene-2-sulfonate.

The salts of the compounds of formula (I) also include the salts with organic or mineral bases, for example the salts of alkali or alkaline earth metals, such as the sodium, potassium and calcium salts, the sodium and potassium salts being preferred, or with an amine such as trometamol, or else the salts of arginine, lysine or any physiologically acceptable amine.

According to the present description and in the claims which follow, halogen atom is understood as meaning a bromine, chlorine or fluorine atom; N-protecting group (also designated by Pr) is understood as meaning a group conventionally used in peptide chemistry for affording temporary protection of the amine group, for example a Boc, Z or Fmoc group or a benzyl group; esterified carboxyl group is understood as meaning an ester which is labile under appropriate conditions, such as, for example, a methyl, ethyl, benzyl or tert-butyl ester.

The nitrogen heterocycles which are described in the definition of the substituents $R_1$ and $R_2$ can also exist in several tautomeric forms, each of which forms part of the invention.

The following abbreviations are used in the description and in the Examples:
Et: ethyl
nBu, tBu: n-butyl, tert-butyl
DMF: dimethylformamide
THF: tetrahydrofuran
DCM: dichloromethane
DCC: dicyclohexylcarbodiimide
NBS: N-bromosuccinimide
DIPEA: diisopropylethylamine
HOBT: hydroxybenzotriazole
AcOH: acetic acid
AcOEt: ethyl acetate
ether: ethyl ether
TFA: trifluoroacetic acid
Z: benzyloxycarbonyl
Boc: tert-butoxycarbonyl
BOP: benzotriazolyloxytrisdimethylaminophosphonium hexafluorophosphate
Fmoc: fluorenylmethoxycarbonyl The present invention further relates to the method of preparing the compounds (I). Said method comprises:
a) reacting a heterocyclic derivative of the formula

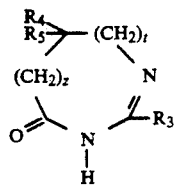

in which z, t, $R_3$, $R_4$ and $R_5$ are as defined above for (I), with a (biphenyl-4-yl)methyl derivative of the formula

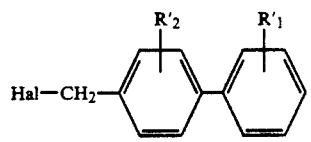

in which Hal is a halogen atom and $R'_1$ and $R'_2$ are respectively either $R_1$ and $R_2$ or a precursor of $R_1$ and/or $R_2$;

b) if appropriate, treating the resulting compound of the formula

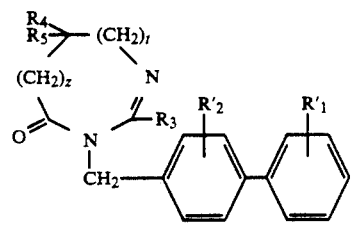

with Lawesson's reagent [2,4-bis(4-methoxyphenyl)-1,3-dithia-2,4-diphosphetane 2,4-disulfide]; and c) treating the compound obtained in a) or in b), of the formula

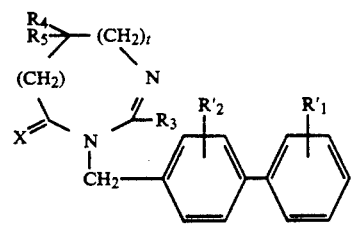

in which X is an oxygen atom or a sulfur atom, to give the compound (I) by conversion of the groups $R'_1$ and/or $R'_2$ to $R_1$ and/or $R_2$ respectively.

The compound 2 is known or is prepared by known methods. For example, it is possible to use the method described by Jacquier et al. (Bull. Soc. Chim. France, 1971, (3), 1040–1051) and to react an alkyl imidate 6 with an amino acid or its ester 5' in accordance with the following reaction scheme:

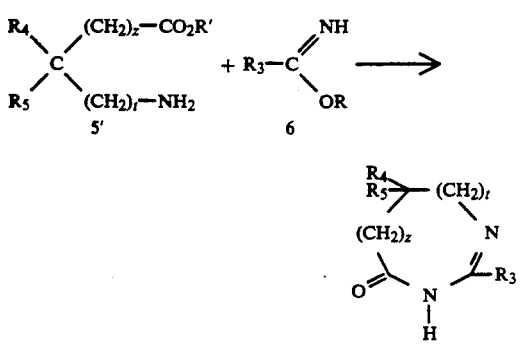

in which R is a $C_1$–$C_4$ alkyl, R' is hydrogen or a $C_1$–$C_4$ alkyl and z, t, $R_3$, $R_4$ and $R_5$ are as defined above.

This reaction is carried out in an acid medium by heating in an inert solvent such as xylene or toluene.

The compounds 5' are known compounds or are prepared by known methods. If $R_4$ and $R_5$ are different, the compounds 5' can be obtained optically pure by using methods of asymmetric synthesis or methods of resolving the racemic mixture, such as those described in Synthesis of Optically Active α-Aminoacids, R. M. Williams, Pergamon Press, 1989.

The (biphenyl-4-yl)methyl derivative (3) is prepared by a method adapted from that described in European patent application 324 377.

Thus the preparation of a compound 3 in which $R'_1$ and/or $R'_2$ is a carboxyl or carboxyester group is described in the patent application cited above.

The methods known in the literature are used to prepare compounds 3 in which $R_1$ and/or $R_2$ have one of the meanings described above for (I). The desired group $R_1$ and/or $R_2$ can also be obtained in the last step of the method described above, starting from the compound 5 in which $R'_1$ and/or $R'_2$ are a carboxyl group or a derivative of a carboxyl group. Such a compound 5 is prepared from a compound 3 in which $R'_1$ and/or $R'_2$ are a group making it possible to prepare $R_1$ and/or $R_2$.

The literature references below may be cited for the preparation of the substituents $R_1$ and/or $R_2$ of the compounds 3 or 5:

5-oxo-1,2,4-oxadiazol-3-yl:
M. A. Perez et al., Synthesis, 1983, 483.
A. R. Katritzky et al., Tetrahedron, 1965, 21, 1681–1692.
K. R. Rao et al., Heterocycles, 1988, 27(3), 683–685.
G. Babu et al., J. Org. Chem., 1976, 41(20), 3233–3237.

This substituent is obtained from the group $C(OC_2H_5)=NCO_2CH_3$; the starting substituent is a carboxyl group, which is converted to a carboxamido group and then to an ethyl carboximidate [R. J. Bergeron et al., J. Org. Chem., 1985, 50(15), 2781].

3-oxo-1,2,4-oxadiazol-5-yl:
A. R. Katritzky et al., Tetrahedron, 1965, 21, 1681–1692.
German patents 2 312 500 and 2 212 797.
O. Tsuge et al., J. Org. Chem., 1980, 45, 5130.

This substituent is obtained from a carboxyl, which is converted to a carboxamido group and then to an isocyanatocarbonyl group.

4,5-dihydro-5-oxoisoxazol-3-yl:
F. De Sarlo et al., Tetrahedron, 1966, 22, 2989–2994.

This substituent is obtained from the group $COCH_2CO_2$—$C_2H_5$, which is prepared from a carboxyl [W. Wierenga et al., J. Org. Chem., 1979, 44, 310–311].

1,2,4-triazol-3-yl:
H. Y. Yale et al., J. Med. Chem., 1966, 9, 42.

This substituent is obtained from the carbonylthiosemicarbazide, which is prepared from a carboxyl group [J. Sandstrom in Advances in Heterocyclic Chemistry (A. R. Katritzky and A. J. Boulton, ed.), Academic Press, 1968, 9, 175].

2-amino-1,3,4-thiadiazol-5-yl: This substituent is also obtained from the above carbonylthiosemicarbazide.

3-amino-1,2,4-oxadiazol-5-yl:
J. Saunders et al., J. Chem. Soc. Chem., 1988, 1618.
This substituent is obtained from the (O-guanidino)carboxylate, which is prepared by reacting 2-hydroxyguanidine with a carboxylic acid in the presence of BOP and DIPEA.

3-oxo-1,2,4-triazol-5-yl:
M. A. Perez et al., Synthesis, 1983, 483.
This substituent is obtained from the group $C(OC_2H_5)=NCO_2CH_3$ by reaction with hydrazine hydrochloride in the presence of an alcoholate such as sodium methylate.

3,5-dioxo-1,2,4-oxadiazol-2-yl:
J. L. Kraus et al., J. Heterocyclic Chem., 1982, 19, 971.
This substituent is obtained from the group $N(OH)$—$CONHCOOC_2H_5$, which is prepared by reacting ethoxycarbonyl isocyanate with a hydroxylamine group, the latter being obtained by reducing a nitro group.

2-oxo-1,3,4-oxadiazol-5-yl:
J. Gante, Chem. Ber., 1965, 98(2), 540–547.
This substituent is prepared from the hydrazine group, which is obtained from a carboxyl group.

In the method according to the invention, step a) is carried out in an inert solvent such as DMF, DMSO or THF, in a basic medium, for example in the presence of potassium hydroxide, potassium carbonate, a metal alcoholate, a metal hydride or triethylamine.

Step b) is carried out by heating under nitrogen in a solvent such as toluene, in accordance with the method described by M. P. Cava et al., Tetrahedron, 1985, 41, 22, 5061.

The compounds (I) according to the invention in which $R_4$ and $R_5$, bonded together, are a group of the formula $(CH_2)_pY(CH_2)_q$ in which Y is an NH group can be prepared by the catalytic hydrogenation of a corresponding compound (I) in which Y is a group N—$R_6$, $R_6$ being a benzyl.

The affinity of the products according to the invention for angiotensin II receptors was studied in a test for the binding of angiotensin II, labeled with iodine 125, to rat liver membrane receptors. The method used is that described by S. Keppens et al. in Biochem. J., 1982, 208, 809–817.

The $IC_{50}$, namely the concentration which gives a 50% displacement of the labeled angiotensin II bound specifically to the receptor, is measured. The $IC_{50}$ of the compounds according to the invention is less than $10^{-6}M$.

Also, the effect of the products according to the invention as angiotensin II antagonists was observed on different animal species in which the reninangiotensin system had been activated beforehand (C. Lacour et al., J. Hypertension, 1989, 7 (suppl. 2), S33–S35).

The compounds according to the invention are active after administration by different routes, especially after oral administration.

No signs of toxicity are observed for these compounds at the pharmacologically active doses.

Thus the compounds according to the invention can be used in the treatment of various cardiovascular complaints, especially hypertension, heart failure and venous insufficiency, as well as in the treatment of glaucoma, diabetic retinopathy and various complaints of the central nervous system, for example anxiety, depression, memory deficiencies or Alzheimer's disease.

The present invention further relates to pharmaceutical compositions containing an effective dose of a compound according to the invention, or of a pharmaceutically acceptable salt, and suitable excipients. Said excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal or rectal administration, the active principles of formula I above, or their salts if appropriate, can be administered to animals and humans in unit forms of administration, mixed with conventional pharmaceutical carriers, for the prophylaxis or treatment of the above disorders or diseases. The appropriate unit forms of administration include forms for oral administration, such as tablets, gelatin capsules, powders, granules and solutions or suspensions to be taken orally, forms for sublingual, buccal, intratracheal or intranasal administration, forms for subcutaneous, intramuscular or intravenous administration and forms for rectal administration. For topical application, the compounds according to the invention can be used in creams, ointments or lotions.

To obtain the desired prophylactic or therapeutic effect, the dose of active principle can vary between 0.01 and 50 mg per kg of body weight per day.

Each unit dose can contain from 0.5 to 1000 mg, preferably from 1 to 500 mg, of active ingredients in combination with a pharmaceutical carrier. This unit dose can be administered 1 to 5 times a day so as to administer a daily dosage of 0.5 to 5000 mg, preferably of 1 to 2500 mg.

When a solid composition is prepared in the form of tablets, the main active ingredient is mixed with a pharmaceutical vehicle such as gelatin, starch, lactose, magnesium stearate, talc, gum arabic or the like. The tablets can be coated with sucrose, a cellulose derivative or other appropriate substances, or else they can be treated so as to have a prolonged or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir or for administration in the form of drops can contain the active ingredient together with a sweetener, which is preferably calorie-free, methylparaben and propylparaben as antiseptics, and also a flavoring and an appropriate color.

The water-dispersible granules or powders can contain the active ingredient mixed with dispersants or wetting agents, or suspending agents such as polyvinylpyrrolidone, as well as with sweeteners or taste correctors.

Rectal administration is effected using suppositories prepared with binders which melt at the rectal temperature, for example cacao butter or polyethylene glycols.

Parenteral administration is effected using aqueous suspensions, isotonic saline solutions or sterile and injectable solutions which contain pharmacologically compatible dispersants and/or wetting agents, for example propylene glycol or butylene glycol.

The active principle can also be formulated as microcapsules, with one or more carriers or additives if appropriate.

In addition to the products of formula I above or one of the pharmaceutically acceptable salts, the compositions of the present invention can contain other active principles such as, for example, tranquilizers or other drugs which can be useful in the treatment of the disorders or diseases indicated above.

Thus the present invention relates to pharmaceutical compositions containing several active principles in association, one being a compound according to the invention and it being possible for the other or others to be a beta-blocking compound, a calcium antagonist, a diuretic, a non-steroidal antiinflammatory or a tranquilizer.

The Examples which follow illustrate the invention without however implying a limitation. The following abbreviations are used in these Examples:

RT denotes room temperature, $KHSO_4$—$K_2SO_4$ denotes an aqueous solution containing 16.6 g of potassium bisulfate and 33.3 g of potassium sulfate per liter. In general, the saline solutions employed are aqueous solutions.

The melting points (m.p.) are given in degrees Celsius; unless indicated otherwise, they are measured without recrystallization of the product.

The purity of the products is checked by thin layer chromatography (TLC) or by HPLC (high performance liquid chromatography). The products are characterized by their NMR spectra run at 200 MHz in deuterated DMSO with tetramethylsilane as the internal reference, unless indicated otherwise.

The following abbreviations are used in the interpretation of the NMR spectra:

s: for singlet
sb: for broad singlet
d: for doublet
t: for triplet
q: for quadruplet
quint: for quintuplet
sext: for sextuplet
m: for unresolved signals or multiplet In addition, im denotes imidazole.

Conventionally, in the compounds illustrated below, the hydrogen atoms are numbered on the biphenyl as shown in the following formula:

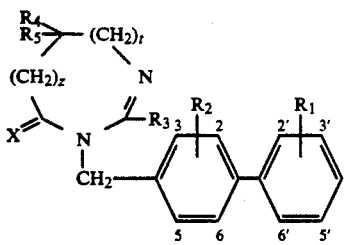

(I)

In the Examples below, z and t are zero.

EXAMPLES 1 AND 2

2-n-Butyl-1-[(2'-(5-oxo-1,2,4-oxadiazol-3-yl)biphenyl-4-yl)methyl]-4-spirocyclopentane-2-imidazolin-5-one

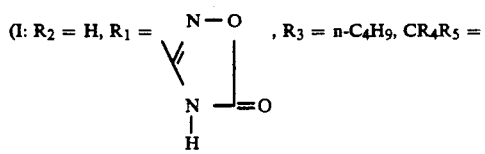

cyclopentane, X = O)

and ethyl 4'-(2-n-butyl-5-oxo-4-spirocyclopentane-2-imidazolin-1-yl)methylbiphenyl-2-(N-methoxycarbonyl)carboximidate

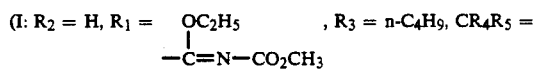

cyclopentane, X = O)

A) 2-n-Butyl-4-spirocyclopentane-2-imidazolin-5-one

The ethyl ester of 1-aminocyclopentanecarboxylic acid is prepared according to Adkins and Billica (J. Amer. Chem. Soc., 1948, 70, 3121).

Ethyl valerimidate is prepared according to Mac Elvain (J. Amer. Chem. Soc., 1942, 64, 1825–1827) and then freed from its hydrochloride by reaction with potassium carbonate and extraction with DCM.

The ethyl ester of 1-aminocyclopentanecarboxylic acid (1.57 g) and ethyl valerimidate (1.56 g) are dissolved in 12 ml of xylene containing 6 drops of acetic acid. After refluxing for 6 and a half hours, the reaction medium is concentrated under vacuum and the residue is then chromatographed on silica gel using a chloroform/methanol/acetic acid mixture (94/4/2; v/v/v) as the eluent. The fraction containing the expected product is evaporated several times in the presence of xylene and then benzene in order to remove the acetic acid. 1.91 g of product are obtained in the form of a thick oil.

IR ($CHCl_3$): 1720 $cm^{-1}$:C=O; 1635 $cm^{-1}$: C=N. Note: The absence of a band between 1500 and 1600 $cm^{-1}$ indicates that, in chloroform solution, the product is an imidazolin-5-one.

NMR spectrum: 0.92 ppm: t:3H:$CH_3$(nBu); 1.35 ppm: sext:2H:$CH_3$—$CH_2$—; 1.50–1.93 ppm: m:10H:$CH_3$—$CH_2$—$CH_2$ and cyclopentane; 2.33 ppm: t:2H:$CH_3$—$CH_2$—$CH_2$—$CH_2$—; 10.7 ppm: m:NH.

Mass spectrum: $MH^+$ = 195.

B) Ethyl 4-methylbiphenyl-2'-(N-methoxycarbonyl)-carboximidate

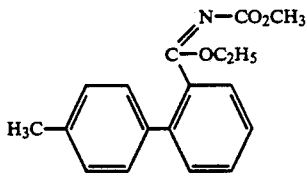

This compound is prepared according to R. J. Bergeron et al., J. Org. Chem., 1985, 50(15), 2781 (preparation of the imidate) and then according to M. A. Perez, Synthesis, 1983, 483.

4'-Methylbiphenyl-2-carboxamide is prepared according to European patent application 253 310.

3.09 g of this compound are dissolved in 100 ml of methylene chloride and treated with 4.43 g of triethyloxonium hexafluorophosphate at a concentration of 90% in ethyl ether, for 24 hours at room temperature. 50 ml of a water/ice mixture are added and the organic phase is extracted and then washed with 50 ml of 1M sodium carbonate and then 20 ml of water. After drying over sodium sulfate, the solution is filtered and concentrated to give an oil, which crystallizes in the cold. This is taken up with 50 ml of hexane and treated with 1.36 ml of methyl chloroformate and 2.06 ml of 2,4,6-trimethylpyridine under reflux of 24 hours. The solid obtained is filtered off and rinsed with hexane. The filtrate is concentrated and purified by chromatography on silica using a hexane/ethyl acetate mixture (6/4; v/v) as the eluent. The oil obtained crystallizes slowly in the cold to give 3.53 g of the expected compound.

M.p.=54°–57° C.

NMR spectrum: 0.9 ppm: t: 3H: $CH_2$—$CH_3$; 2.3 ppm: s: 3H: $C_6H_4$—$CH_3$; 3.5 ppm: s: 3H: $CO_2$—$CH_3$; 3.9 ppm: q: 2H: —$CH_2$—$CH_3$.

C) Ethyl 4-bromomethylbiphenyl-2'-(N-methoxycarbonyl)carboximidate

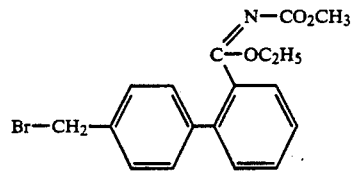

1.008 g of the compound obtained in the previous step are dissolved in 40 ml of carbon tetrachloride and then treated with 610 mg of N-bromosuccinimide and 15 mg of azobisisobutyronitrile for 3 hours under reflux. After cooling, the reaction medium is filtered and the filtrate is concentrated. The expected compound is obtained in the form of an oil with a purity of 70%.

NMR spectrum: 0.9 ppm: t: 3H: $CH_2$—$CH_3$; 3.55 ppm: s: 3H: $CO_2CH_3$; 3.9 ppm: q: 2H: —$CH_2$—$CH_3$; 4.8 ppm: s: 2H: —$CH_2$—Br.

D) Ethyl 4'-(2-n-butyl-5-oxo-4-spirocyclopentane-2-imidazolin-1-yl)methylbiphenyl-2-(N-methoxycarbonyl)carboximidate 781 mg of the imidazolinone prepared in step A are used as a solution of the hydrochloride in 20 ml of dimethylformamide and treated under nitrogen with 223 mg of an 80% suspension of sodium hydride in oil. After stirring for 15 minutes at room temperature, a solution of the bromine derivative obtained in step C (1.3 g) in 10 ml of dimethylformamide is added in portions and the mixture is stirred for 2 hours. After concentration of the reaction medium, the oil obtained is taken up in 100 ml of ethyl acetate and washed with twice 30 ml of a solution of $KHSO_4$—$K_2SO_4$, 30 ml of a saturated solution of sodium chloride, 30 ml of a saturated solution of sodium hydrogencarbonate and another 30 ml of a saturated solution of sodium chloride. After drying over sodium sulfate, the solution is concentrated and the oil obtained is purified by chromatography on silica using a heptane/ethyl acetate mixture (8/2 then 7/3; v/v) as the eluent. The pure fractions are concentrated to give the expected product in the form of a yellow oil: m = 1.1 g.

NMR spectrum: 0.9 ppm: quint: 6H: $CH_2$—$CH_3$ (OEt), $CH_3$ (nBu); 1.3 ppm: sext: 2H: $CH_2$—$CH_3$ (nBu); 1.55 ppm: quint: 2H: $CH_2$—$CH_2$—$CH_3$ (nBu); 1.75-2 ppm: m: 8H: cyclopentane; 2.40 ppm: t: 2H: $CH_2$—$CH_2$—$CH_3$; 3.55 ppm: s: 3H: $CO_2$—$CH_3$; 3.95 ppm: q: 2H: $CH_2$—$CH_3$ (OEt); 4.8 ppm: s: 2H: $CH_2$—$C_6H_4$—; 7.2-7.7 ppm: m: 8H: aromatic.

E) This step is carried out according to M. A. Perez, Synthesis, 1983, 483.

2-n-Butyl-1-[(2'-(5-oxo-1,2,4-oxadiazol-3-yl)biphenyl-4-yl)methyl]-4-spirocyclopentane-2-imidazolin-5-one 76 mg of hydroxylamine hydrochloride in 5 ml of methanol are treated at room temperature for 15 minutes with 62 mg of 95% sodium methylate. 490 mg of the compound obtained in step D in 5 ml of methanol are added. After refluxing overnight, the reaction medium is concentrated and taken up with dichloromethane. An insoluble material is removed and the filtrate is concentrated and then chromatographed on silica using a heptane/ethyl acetate mixture (4/6 then 3/7; v/v) as the eluent. The pure fractions are combined and concentrated to give a white solid, which is taken up with hexane, filtered off and dried.

m = 340 mg.

M.p. = 157°-160° C.

NMR spectrum: 0.9 ppm: t: 3H: $CH_3$ (nBu); 1.3 ppm: sext: 2H: $CH_2$—$CH_3$ (nBu); 1.5 ppm: quint: 2H: $CH_2$—$CH_2$—$CH_3$ (nBu); 1.75-1.95 ppm: m: 8H: cyclopentane; 2.35 ppm: t: 2H: $CH_2$—$CH_2$—$CH_2$—$CH_3$ (nBu); 4.75 ppm: s: 2H: $CH_2$—$C_6H_4$—; 7.2-7.8 ppm: m: 8H: aromatic; 12.4 ppm: s: 1H: NH.

EXAMPLES 3 AND 4

1-[(2'-(4,5-Dihydro-5-oxoisoxazol-3-yl)biphenyl-4-yl)methyl]-2-n-propyl-4-spirocyclohexane-2-imidazolin-5-one

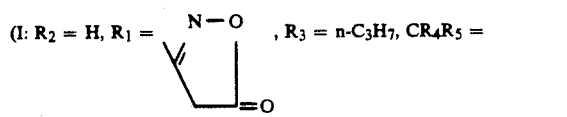

(I: $R_2$ = H, $R_1$ = [structure], $R_3$ = n-$C_3H_7$, $CR_4R_5$ = cyclohexane, X = O)

and ethyl 3-[4'-(2-n-propyl-5-oxo-4-spirocyclohexane-2-imidazolin-1-yl)methylbiphenyl-2-yl]-3-oxopropionate (I: $R_2$ = H, $R_1$ = -$COCH_2CO_2C_2H_5$, $R_3$ = n-$C_3H_7$, $CR_4R_5$ = cyclohexane, X = O)

A) Ethyl butyrimidate hydrochloride

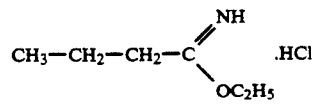

This compound is prepared according to McElvain (J. Amer. Chem. Soc., 1942, 64, 1825-1827).

23 ml of butyronitrile are added at 0° C. to a solution of 10.6 g of gaseous hydrogen chloride in 20 ml of anhydrous ethanol and the reaction medium is then left to stand for 4 days at 0° C. and poured into 200 ml of anhydrous ether at 0° C., with stirring; the precipitate formed is filtered off, washed with ether and then dried under vacuum to give 25.8 g of the expected product.

B) Ethyl butyrimidate 16 g of the imidate obtained in step A are dissolved in 100 ml of dichloromethane and 50 ml of water, and 15 g of potassium carbonate are added. After decantation, the dichloromethane is dried over potassium carbonate and then evaporated off to dryness without heating.

C) Ethyl ester of 1-aminocyclohexanecarboxylic acid

1-Aminocyclohexanecarboxylic acid is commercially available. 15 g of this amino acid are added at 0° C. to a solution of 23 g of gaseous hydrogen chloride in 150 ml of anhydrous ethanol. The reaction medium is refluxed for 5 hours and then concentrated to dryness and taken up with ether. The white solid obtained is filtered off, washed with ether and then dissolved in a mixture of 300 ml of ether and 100 ml of water. The pH is brought to 9 by adding a solution of potassium carbonate. The organic phase is decanted, washed with a saturated solution of sodium chloride, dried over sodium sulfate and then evaporated to dryness to give 14 g of the expected product in the form of an oil.

D) 2-n-Propyl-4-spirocyclohexane-2-imidazolin-5-one 14 g of the product obtained in step C are dissolved in 200 ml of xylene containing 0.6 ml of acetic acid. Half of the imidate obtained in step B is added and the mixture is heated to the reflux point. Half of the remaining imidate is added after 1 and a half hours and the final quarter is then added after 4 hours. After a total of 7 hours under reflux, the medium is evaporated to dryness. The solid obtained is taken up in hexane, filtered off, washed with ether and then dried.

10.3 g of the expected imidazolinone are obtained.

M.p. = 124°-125° C.

IR ($CHCl_3$): 1715 cm$^{-1}$: C=O; 1635 cm$^{-1}$: C=N.

Note: According to the values of the IR bands, the compound present in solution is indeed an imidazoline-5-one.

E) 2-n-Propyl-4-spirocyclohexane-1-[(2'-tertbutoxycarbonylbiphenyl-4-yl)methyl]-2-imidazolin-5-one 970 mg of the imidazolinone obtained in step D are added to 0.24 g of an 80% suspension of sodium hydride in oil, suspended in 10 ml of dimethylformamide. After stirring for 20 minutes under nitrogen, 1.91 g of 4-bromomethyl-2'-tert-butoxycarbonylbiphenyl, prepared according to European patent application 324 377, are added over 5 minutes. After stirring for 1 hour, the medium is concentrated to half its volume under vacuum and taken up with 100 ml of ethyl acetate and then 20 ml of water. The organic phase is decanted, washed with a saturated solution of sodium chloride, dried over sodium sulfate and then concentrated under vacuum. The residue is chromatographed on silica using an ethyl acetate/toluene mixture as the eluent to give 2.10 g of the expected product in the form of a wax.

IR (CHCl$_3$): 1705-1715 cm$^{-1}$: C=O; 1635 cm$^{-1}$: C=N.

Analysis of the NMR spectrum confirms the structure.

F) 1-[(2'-Carboxybiphenyl-4-yl)methyl]-2-n-propyl-4-spirocyclohexane-2-imidazolin-5-one 1.25 g of the tert-butyl ester obtained in step E are stirred for 45 minutes in a mixture of 11 ml of dichloromethane and 15 ml of trifluoroacetic acid. After concentration under vacuum, the residue is taken up in ether. The solid formed is filtered off, washed with ether and then dried to give 1.04 g of a white solid.

M.p. = 170°-172° C.

NMR spectrum: 7.10-7.80 ppm: m:8H:aromatic; 4.90 ppm: s:2H:CH$_2$—C$_6$H$_4$—; 2.45 ppm: t:2H:CH$_3$—CH$_2$—CH$_2$—; 1.40-1.80 ppm: m:12H:spirocyclohexane+CH$_3$—CH$_2$—CH$_2$—; 0.90 ppm: t:3H:CH$_3$—CH$_2$—CH$_2$—.

1.60 g of the trifluoroacetate obtained above are dissolved in 150 ml of ethyl acetate plus 20 ml of water. 1N sodium hydroxide is added to bring the pH to 5.0. The organic phase is decanted, washed with a saturated solution of sodium chloride, dried over sodium sulfate and then evaporated to dryness. The solid residue is taken up in ethyl ether, filtered off and dried.

m = 1.14 g.

M.p. = 208°-210° C.

G) Ethyl 3-[4'-(2-n-propyl-5-oxo-4-spirocyclohexane-2-imidazolin-1-yl)methylbiphenyl-2-yl]-3-oxopropionate (I: R$_2$=H, R$_1$=—COCH$_2$CO$_2$C$_2$H$_5$, R$_3$=n—C$_3$H$_7$, CR$_4$R$_5$=cyclohexane, X=O)

This compound is prepared from the acid obtained in step F in accordance with the method described by W. Wierenga and H. I. Skulnick in J. Org. Chem., 1979, 44, 310-311.

0.9 ml of thionyl chloride is added to 500 mg of the acid obtained in the previous step, suspended in 7 ml of dichloromethane. After 1 hour 20 minutes, the solution obtained is concentrated under vacuum and then evaporated twice with benzene. The acid chloride is obtained in the form of a white foam. 3.75 ml of 1.6M n-butyllithium in hexane are added at −70° C. over 5 minutes to 402 mg of ethyl monomalonate in 6 ml of THF, the temperature is allowed to rise to −5° C., the mixture is then cooled again to −65° C. and a solution of the acid chloride in 5 ml of THF is added over 10 minutes. The temperature is allowed to rise to 0° C. over 1 hour and the mixture is stirred for 20 hours at 0° C. The reaction medium is poured into 100 ml of ethyl acetate containing 9 ml of 1N hydrochloric acid, the mixture is stirred for 10 minutes and the pH is then brought to 8.0 by adding 1N sodium hydroxide. The organic phase is decanted, washed with a saturated solution of sodium chloride, dried over sodium sulfate and then concentrated under vacuum. The residue is chromatographed on silica using an ethyl acetate/toluene mixture as the eluent to give 300 mg of the expected product in the form of an oil.

IR (CHCl$_3$): 1710-1730 cm$^{-1}$: 3 carbonyls in the form of a broad band; 1630 cm$^{-1}$: C=N of the imidazolinone.

NMR spectrum: 7.10-7.70 ppm: m:8H:aromatic; 4.65 ppm: s:2H:CH$_2$—C$_6$H$_4$—; 3.95 ppm: q:2H:CH$_2$ of the ethyl ester; 3.60 ppm: s:2H:CH$_2$ of the β-ketoester; 2.25 ppm: t:2H:CH$_3$—CH$_2$—CH$_2$; 1.20-1.70 ppm: m:12H:10H of the cyclohexane+2H (CH$_3$—CH$_2$—CH$_2$—); 1.05 ppm: t:3H:CH$_3$ of the ethyl ester; 0.80 ppm: t:3H:CH$_3$—CH$_2$—CH$_2$.

Note: According to the following observations, part of the product (about 15%) is in the enol form:

3.60 ppm, the singlet has an integration of less than 2H 7.20 ppm: s:ethyl H of the enol form the signals of the ethyl of the ethyl ester are slightly distorted.

H) 1-[(2'-(4,5-Dihydro-5-oxoisoxazol-3-yl)biphenyl-4-yl)methyl]-2-n-propyl-4-spirocyclohexane-2-imidazolin-5-one This compound is prepared in accordance with the method described by F. De Sarlo et al., Tetrahedron, 1966, 22, 2989-2994.

300 mg of the product obtained in the previous step are dissolved in 3 ml of pyridine, 52 mg of hydroxylamine hydrochloride are added and the mixture is heated at 100° C. for 2 hours 45 minutes. The reaction medium is taken up with 100 ml of ethyl acetate and 15 ml of water; the organic phase is decanted, washed with a saturated solution of sodium chloride, dried over sodium sulfate and then concentrated under vacuum. The residue is chromatographed on silica using an ethyl acetate/methanol/acetic acid mixture (99.25/0.5/0.25; v/v/v) as the eluent. 100 mg of product are obtained after crystallization from an ether/hexane mixture.

M.p. = 165°-170° C. with decomposition.

The product is identified by its spectra.

IR (KBr): 1805 cm$^{-1}$: C=O:isoxazolone.

NMR spectrum (CDCl$_3$): 7.20-7.90 ppm: m:8H:aromatic; 4.80 ppm: s:2H:CH$_2$—C$_6$H$_4$—; 3.05 ppm: s:2H:CH$_2$ of the isoxazolone; 2.40 ppm: t:2H:CH$_3$—CH$_2$—CH$_2$; 1.40-2.00 ppm: m:12H:10H of the cyclohexane and CH$_3$—CH$_2$—CH$_2$—; 1.00 ppm: t:3H:CH$_3$ (n-propyl).

Mass spectrum: MH$^+$: 444.

EXAMPLE 5

4'-(2-n-Butyl-5-oxo-4-spirocyclopentane-2-imidazolin-1-yl)methylbiphenyl-2-carbonylthiosemicarbazide (I: R$_2$=H, R$_1$=—CONH—NH—CS—NH$_2$, R$_3$=n—C$_4$H$_9$, CR$_4$R$_5$=cyclopentane, X=O)

2-n-Butyl-4-spirocyclopentane-2-imidazolin-5-one is described in Examples 1 and 2, step A.

A) 2-n-Butyl-4-spirocyclopentane-1-(2'-tert-butoxycarbonylbiphenyl-4-yl)methyl-2-imidazolin-5-one 970 mg of the product obtained in Example 1, step A), are dissolved in 10 ml of dimethylformamide. 270 ml of sodium methylate are added and the mixture is stirred for 15 minutes at room temperature. 2.08 g of 4-bromomethyl-2'-tert-butoxycarbonylbiphenyl are added to the suspension and then, after 30 minutes, the mixture is heated at 40° C. under nitrogen for 3 and a half hours. The reaction medium is taken up with a mixture containing 100 ml of ethyl acetate, 10 ml of water and 1 ml of a saturated solution of sodium bicarbonate. The organic phase is washed with a saturated solution of sodium chloride and then dried over sodium sulfate and evaporated to dryness. The residue is chromatographed on silica gel using an ethyl acetate/toluene mixture (1/2; v/v) as the eluent to give 1.25 g of the expected product, which crystallizes.

M.p. = 63°-66° C.

B) 2-n-Butyl-1-[(2'-carboxybiphenyl-4-yl)methyl]-4-spirocyclopentane-2-imidazolin-5-one trifluoroacetate 1.22 g of the product obtained in the previous step are stirred for 40 minutes in a solution containing 6 ml of dichloromethane and 8 ml of TFA. After concentration under vacuum, the residue is taken up in ethyl ether; the white precipitate formed is filtered off, washed with ether and then dried under vacuum to give 1.15 g of the expected product.

M.p.=176°-178° C.

NMR spectrum: 0.78 ppm: t:3H:CH$_3$(nBu); 1.25 ppm: sext:2H:CH$_3$—CH$_2$; 1.50 ppm: quint:2H:CH$_3$—CH$_2$—CH$_2$; 1.75-2.00 ppm: m:8H:cyclopentane; 2.65 ppm: t:2H:CH$_3$—CH$_2$—CH$_2$—CH$_2$—; 4.83 ppm: s:2H:CH$_2$—C$_6$H$_4$—; 7.20-7.75 ppm: m:8H:aromatic.

Mass spectrum: MH+: 405.

C) 4-(2-n-Butyl-5-oxo-4-spirocyclopentane-2-imidazolin-1-yl)methylbiphenyl-2'-carbonylthiosemicarbazide 101 mg of the acid prepared in the previous step, 25 mg of thiosemicarbazide, 5 ml of dimethylformamide and 111 g of BOP are mixed with a sufficient amount of DIPEA to maintain a pH of 8. After stirring for 3 hours at room temperature, the mixture is evaporated and the residue is taken up with ethyl acetate and washed with water, sodium carbonate, water and then a saturated solution of sodium chloride. The solid obtained is chromatographed on silica using a dichloromethane/methanol mixture (100/3; v/v) as the eluent.

The product obtained solidifies in isopropyl ether.

M.p.=124°-126° C.

NMR spectrum: 0.75 ppm: t:3H:CH$_3$—CH$_2$—CH$_2$—CH$_2$—; 1.25 ppm: sext:2H:CH$_3$—CH$_2$—CH$_2$—CH$_2$—; 1.45 ppm: quint:2H:CH$_3$—CH$_2$—CH$_2$—CH$_2$—; 1.55-1.90 ppm: m:8H:cyclopentane; 2.3 ppm: t:2H:CH$_3$—CH$_2$—CH$_2$—CH$_2$—; 4.7 ppm: s:2H:N—CH$_2$—C$_6$H$_4$—; 6.7 and 7.85 ppm: 2sb:2 times H:—CS—NH$_2$; 7.15-7.8 ppm: m:8H:aromatic; 9.3 and 10.0 ppm: 2s:2 times H:NH—NH.

EXAMPLE 6

1-[(2'-(2-Amino-1,3,4-thiadiazol-5-yl)biphenyl-4-yl)methyl]-2-n-butyl-4-spirocyclopentane-2-imidazolin-5-one

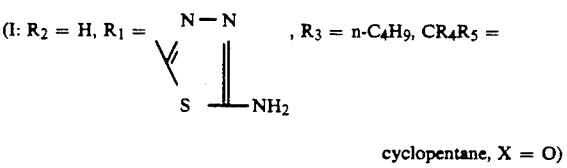

cyclopentane, X = O)

This compound is prepared by using the method described by J. Sandstrom in Advances in Heterocyclic Chemistry (ed. A. R. Katrizky and A. J. Boulton, Academic Press, 1968, 9, 175).

350 mg of the compound prepared in the previous Example and 10 drops of methanesulfonic acid are mixed in 50 ml of toluene and the mixture is refluxed for 18 hours in a round-bottomed flask equipped with a water separator. A 10% solution of sodium carbonate is added, extraction is then carried out with an ethyl acetate/toluene mixture and the extract is chromatographed on a silica column using a dichloromethane/methanol/acetic acid mixture (98/1/1; v/v/v) as the eluent. The product obtained is dissolved in ethyl ether and washed with a 10% solution of sodium carbonate, water and a saturated solution of sodium chloride.

140 mg of the expected product, melting at between 90° and 100° C., are collected.

NMR spectrum: 0.9 ppm: t: 3H: —CH$_2$—CH$_2$—CH$_2$—CH$_3$; 1.30 ppm: sext: 2H: —CH$_2$—CH$_2$—CH$_2$—CH$_3$; 1.55 ppm: quint: 2H: —CH$_2$—CH$_2$—CH$_2$—CH$_3$; 1.7-2 ppm: m: 8H: cyclopentane; 2.4 ppm: t: 2H: —CH$_2$—CH$_2$—CH$_2$—CH$_3$; 4.8 ppm: s: 2H: N—CH$_2$—C$_6$H$_4$—; 7.2 ppm: 2H: NH$_2$; 7.2-7.9 ppm: m: 8H: aromatic.

EXAMPLE 7

4'-(2-n-Butyl-5-oxo-4-spirocyclopentane-2-imidazolin-1-yl)methylbiphenyl-2-carbonyloxyguanidine (I: R$_1$=COON=C(NH$_2$)$_2$, R$_2$=H, R$_3$=n—C$_4$H$_9$, CR$_4$R$_5$=cyclopentane, X=O)

Hydroxyguanidine hemisulfate is prepared according to J. Biol. Chem., 1959, 1481.

A mixture containing 1.036 g of 2-n-butyl-1[(2'-carboxybiphenyl-4-yl)methyl]-4-spirocyclopentane-2-imidazolin-5-one trifluoroacetate, prepared in Example 5, step B), 496 mg of 2-hydroxyguanidine hemisulfate, 50 ml of dimethylformamide, 888 mg of BOP and a sufficient amount of DIPEA to maintain a pH of 9-10 is stirred at room temperature for 18 hours. The solvents are evaporated off and the residue is taken up with ethyl acetate and washed with water, a solution of sodium carbonate, water and a saturated solution of sodium chloride. The product obtained is purified by chromatography on silica using a dichloromethane/methanol mixture (100/2.5; v/v) as the eluent to give 285 mg of the expected product in the form of an amorphous powder melting at between 85° C. and 95° C.

NMR spectrum: 0.9 ppm: t: 3H: CH$_3$—CH$_2$—CH$_2$—CH$_2$—; 1.35 ppm: sext: 2H: CH$_3$—CH$_2$—CH$_2$—; 1.6 ppm: quint: 2H: CH$_3$—CH$_2$—CH$_2$—; 1.7-2 ppm: m: 8H: cyclopentane; 2.4 ppm: t: 2H: CH$_3$—CH$_2$—CH$_2$—CH$_2$—; 4.8 ppm: s: 2H: N—CH$_2$—C$_6$H$_4$—; 4.9 ppm: s: 2H: NH$_2$; 5.1 ppm: s: 2H: NH$_2$; 7.2-7.4 ppm: AA', BB' system (J=8.5 Hz): 4H: N—CH$_2$—C$_6$H$_4$; 7.4-7.9 ppm: m: 4H: N—CH$_2$—C$_6$H$_4$—C$_6$H$_4$.

EXAMPLE 8

1-[(2'-(3-Amino-1,2,4-oxadiazol-5-yl)biphenyl-4-yl)methyl]-2-n-butyl-4-spirocyclopentane-2-imidazolin-5-one

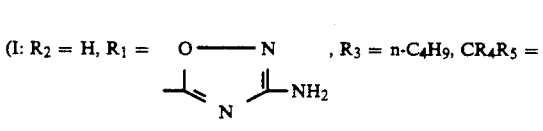

cyclopentane, X = O)

This compound is prepared by using a method modified from that described by J. Saunders et al., J. Chem. Soc., Commun., 1988, 1618.

340 mg of the compound prepared in the previous Example are placed in a test tube and heated in an oil bath at 150° C. for 1 hour. After cooling, it is taken up with dichloromethane, dried over sodium sulfate and then filtered and evaporated. The residue obtained is chromatographed on silica using a dichloromethane/methanol mixture (98/2; v/v) as the eluent. 148 mg of the expected product are recovered.

M.p.=156°-158° C.

NMR spectrum: 0.9 ppm: t: 3H: CH$_3$—CH$_2$—CH$_2$—CH$_2$—; 1.3 ppm: sext: 2H: CH$_3$—CH$_2$—CH$_2$—; 1.5 ppm: quint: 2H: CH$_3$—CH$_2$—CH$_2$—; 1.7-2 ppm: m: 8H: cyclopentane; 2.4 ppm: t: 2H: CH$_3$—CH$_2$—CH$_2$—CH$_2$—; 4.8 ppm: s: 2H:

N—CH$_2$—C$_6$H$_4$—; 6.3 ppm: s: 2H: NH$_2$; 7.2–7.35 ppm: AA', BB' system: 4H: N—CH$_2$—C$_6$H$_4$; 7.5–8 ppm: m: 4H: N—CH$_2$—C$_6$H$_4$—C$_6$H$_4$

EXAMPLE 9

2-n-Butyl-4-spirocyclopentane-1-[(2'-(1,2,4-triazol-3-yl)biphenyl-4-yl)methyl]-2-imidazolin-5-one

(I: R$_2$ = H, R$_1$ = N—N (triazole), R$_3$ = n-C$_4$H$_9$, CR$_4$R$_5$ = cyclopentane, X = O)

A) Preparation of 4'-bromomethyl-2-(trityl-1,2,4triazol 3-yl)biphenyl a) 4'-Methylbiphenyl-2-carbonylthiosemicarbazide

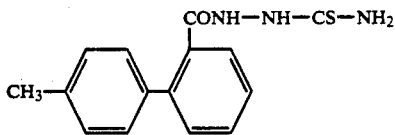

A mixture containing 6.4 g of 4'-methylbiphenyl-2-carboxylic acid, 3.0 g of thiosemicarbazide, 30 ml of dimethylformamide, 13.3 g of BOP and DIPEA to maintain a basic pH (pH 8–9) is stirred for 1 day at room temperature. It is concentrated, washed with water and extracted with ethyl acetate and 7.2 g of the expected product are isolated.

b) 4'-Methyl-2-(5-mercapto-1,2,4-triazol-3-yl)biphenyl

This compound is prepared in accordance with the method described by H. L. Yale et al., J. Med. Chem., 1966, 9, 42.

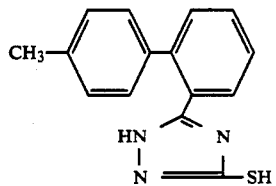

6.3 g of the product obtained in step Aa) and 1.16 g of sodium hydroxide are mixed in 38 ml of water and the mixture is refluxed for 1 hour. After extraction with ether, the aqueous phase is acidified with acetic acid; after filtration, the expected product is obtained in the form of a white solid.

m=5.4 g.
M.p.=250° C.

c) 4'-Methyl-2-(1,2,4-triazol-3-yl)biphenyl 4.7 g of the compound obtained in the previous step are placed in 100 ml of ethanol in the presence of Raney nickel and refluxed for 48 hours. The reaction medium is filtered and then concentrated to give 4 g of the expected product.

M.p.=146° C.

d) 4'-Methyl-2-(trityl-1,2,4-triazol-3-yl)biphenyl 3.8 g of the product obtained in the previous step are refluxed for 8 hours in 100 ml of dichloromethane in the presence of 7.8 g of trityl chloride and 4.8 ml of triethylamine. The reaction medium is concentrated, washed with water and extracted with ethyl acetate. The crude product isolated is recrystallized from hexane. 7.7 g of the expected product are isolated.

M.p.=120°–122° C.

Note: The substitution position of the trityl was not determined.

e) 4'-Bromomethyl-2-(trityl-1,2,4-triazol-3-yl)biphenyl 150 ml of carbon tetrachloride containing 7.45 g of the product obtained in the previous step, 2.85 g of N-bromosuccinimide and 300 mg of benzoyl peroxide are refluxed for 3 hours. The reaction medium is filtered and then concentrated to give 11.25 g of the crude product, which is used as such in the next step.

B) Preparation of the final product a) 2-n-Butyl-4-spirocyclopentane-1-[(2'-(trityl-1,2,4-triazol-3-yl)biphenyl-4-yl)methyl[-2-imidazolin-5-one A mixture containing 500 mg of the imidazolinone prepared in Example 1, step A, 129 mg of an 80% suspension of sodium hydride and 10 ml of dimethylformamide is stirred at room temperature for 30 minutes and 1.7 g of the compound prepared in step A of the present Example and 10 ml of dimethylformamide are then added. After stirring for 5 hours at room temperature, the mixture is concentrated and the residue is then taken up with ethyl acetate, washed with water, dried over sodium sulfate, filtered and then concentrated under reduced pressure. The residue is chromatographed on silica using a dichloromethane/ethyl acetate mixture (9/1; v/v) as the eluent to give 700 mg of the expected product.

b) 2-n-Butyl-4-spirocyclopentane-1-[(2'-(1,2,4-triazol-3-yl)biphenyl-4-yl)methyl]-2-imidazolin-5-one 700 mg of the product obtained in step Ba) in 8 ml of methanol and 0.6 ml of 4 N hydrochloric acid are stirred at room temperature for 6 hours. The reaction medium is concentrated and the residue is then taken up with 2 N sodium hydroxide and extracted with ether. The aqueous phase is acidified with 1 N hydrochloric acid and then extracted with ethyl acetate.

Finally, the extract is chromatographed on silica using a dichloromethane/methanol mixture (97/3; v/v) as the eluent to give 290 mg of the expected product.

M.p.=87° C.

NMR spectrum: 0.7 ppm: t: 3H: CH$_3$—CH$_2$—CH$_2$—CH$_2$—; 1.2 ppm: sext: 2H: CH$_3$—CH$_2$—CH$_2$—CH$_2$—; 1.4 ppm: quint: 2H: CH$_3$—CH$_2$—CH$_2$—CH$_2$—; 1.5–1.9 ppm: m: 8H: cyclopentane; 2.2 ppm: t: 2H: CH$_3$—CH$_2$—CH$_2$—CH$_2$—; 4.6 ppm: s: 2H: N—CH$_2$—C$_6$H$_4$—; 6.9–7.1 ppm: AA', BB' system: 4H: N—CH$_2$—C$_6$H$_4$; 7.3–7.8 ppm: m: 4H: N—CH$_2$—C$_6$H$_4$—C$_6$H$_4$; 8.1 ppm: s: 1H: H (triazole).

EXAMPLE 10

4'-(2-n-Butyl-5-oxo-4-spirocyclopentane-2-imidazolin-1-yl)methylbiphenyl-2-carbonylsemicarbazide (I: R$_1$=CONH—NH—CO—NH$_2$, R$_2$=H, R$_3$=n—C$_4$H$_9$, CR$_4$R$_5$=cyclopentane, X=O)

The 2-imidazolin-5-one prepared in Example 5, step B, is used in the form of the free base; 320 mg of this compound are dissolved in 7 ml of DMF and treated with 390 mg of BOP, 90 mg of semicarbazide hydrochloride and 272 µl of DIPEA. The reaction mixture is stirred for 1 hour at room temperature, the pH being maintained at 7 by adding DIPEA. The reaction medium is concentrated and the oil obtained is taken up with 100 ml of ethyl acetate and washed with 50 ml of a saturated solution of sodium chloride, twice 20 ml of a saturated solution of sodium hydrogencarbonate and then 20 ml of a saturated solution of sodium chloride. It is dried over sodium sulfate and then filtered and concentrated. 330 mg of the expected product are obtained after recrystallization from an ethyl ether/hexane mixture.

NMR spectrum: 0.9 ppm: t:3H:CH₃ (nBu); 1.4 ppm: sext:2H:CH₂—CH₃; 1.6 ppm: quint:2H:CH₂—CH₂—CH₃; 1.7-2.00 ppm: m:8H:cyclopentane; 2.45 ppm: t:2H:CH₂—CH₂—CH₂—CH₃; 4.8 ppm: s:2H:CH₂—C₆H₄—; 5.95 ppm: s:2H:CONH₂; 8.0 ppm: s:1H:CONH; 10.0 ppm: s:1H:CONH.

EXAMPLE 11

2-n-Butyl-1-[(2'-(3-oxo-1,2,4-oxadiazol-5-yl)biphenyl-4-yl)methyl]-4-spirocyclopentane-2-imidazolin-5-one

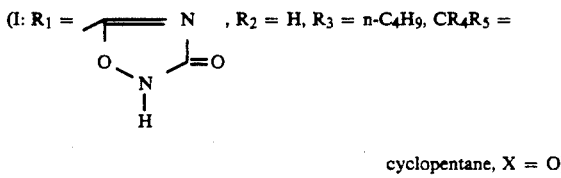

cyclopentane, X = O)

A) 1-[(2'-Carbamoylbiphenyl-4-yl)methyl]-2-n-butyl-4-spirocyclopentane-2-imidazolin-5-one The 2-imidazolin-5-one prepared in Example 5, step B, is used in the form of the free base. 2.65 g of this compound are dissolved in 30 ml of dioxane and 10 ml of DMF and treated with 3.19 g of BOP and 1.24 ml of DIPEA for 1 hour at room temperature. This solution is added in portions at 0° C. to a solution containing 10 ml of dioxane and 20 ml of 20% aqueous ammonia. The mixture is left for 1 hour at 0° C. and then for 2 hours at room temperature. It is concentrated to dryness, the residue is taken up with ethyl acetate and a precipitate of HOBT is removed. The filtrate is washed with water, a saturated solution of sodium hydrogencarbonate, a saturated solution of sodium chloride, a solution of KHSO₄—K₂SO₄ and a saturated solution of sodium chloride. The organic phase is concentrated and taken up with an ethyl ether/hexane mixture. The white solid obtained is filtered off and dried.

m = 2.55 g.
M.p. = 115°-120° C.

B) 2-n-Butyl-1-[(2'-isocyanatocarbonylbiphenyl-4-yl)methyl]-4-spirocyclopentane-2-imidazolin-5-one This compound is prepared according to A. J. Speziale, J. Org. Chem., 1965, 30, 4306. (I: R₁=—CON=C=O, R₂=H, R₃=n—C₄H₉, CR₄R₅=cyclopentane, X=O).

1 g of the amide prepared in the previous step is placed in 15 ml of 1,2-dichloroethane. 300 μl of oxalyl chloride are added at 0° C. and the mixture is then allowed to return to room temperature and refluxed for 6 hours. After concentration to dryness, the black foam is used as such in the next step.

C) 2-n-Butyl-1-[(2'-(3-oxo-1,2,4-oxadiazol-5-yl)biphenyl-4-yl)methyl]-4-spirocyclopentane-2-imidazolin-5-one The product obtained above is treated with 1 ml of trimethylsilyl azide in 10 ml of xylene for 4 hours at 120° C. and concentrated to dryness. 10 ml of ethanol are added, the mixture is stirred for 30 minutes and concentrated to dryness and the residue is then triturated in methanol. The brown solid obtained is filtered off and then rinsed with methanol and ethyl ether and dried.

m = 170 mg.
M.p. = 192°-195° C.
Mass spectrum: MH⁺: 445.

NMR spectrum: 0.85 ppm: t:3H:CH₃ (nBu); 1.25 ppm: sext:2H:CH₃—CH₂; 1.6 ppm: quint:2H:CH₃—CH₂—CH₂; 1.7-2.0 ppm: m:8H:cyclopentane; 2.4 ppm: t:2H:CH₃—CH₂—CH₂—CH₂—; 4.8 ppm: s:2H:CH₂—C₆H₄—; 7.2-8.0 ppm: m:8H:aromatic.

EXAMPLE 12

(R,S)-2-n-Butyl-4-cyclohexyl-4-methyl-1-[(2'-(5-oxo-1,2,4-oxadiazol-3-yl)biphenyl-4-yl)methyl]-2-imidazolin-5-one

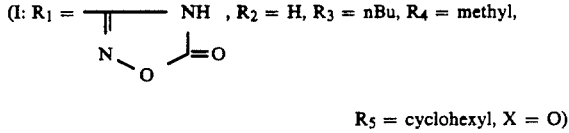

R₅ = cyclohexyl, X = O)

A) 5-Cyclohexyl-5-methylhydantoin

This compound is prepared according to J. Org. Chem., 1960, 25, 1920-1924.

50 g of cyclohexyl methyl ketone, dissolved in 400 ml of 95° alcohol, are added over 30 minutes to 29.4 g of sodium cyanide and 192 g of ammonium carbonate in 400 ml of water. The mixture is heated at 55°-60° C. for 4 hours and then evaporated to half its volume under vacuum and left overnight at +4° C. The precipitate formed is filtered off, washed with water and then dried under vacuum over phosphorus pentoxide to give 65.5 g of the expected hydantoin, which is identified by its IR and NMR spectra.

M.p. = 220° C.

B) (R,S)-2-Amino-2-cyclohexylpropionic acid

This compound is prepared according to J. Org. Chem., 1960, 25, 1920-1924.

A mixture containing 7 g of the hydantoin prepared in the previous step and 28 g of barium hydroxide octahydrate in 150 ml of water is heated at 160° C. for 5 hours in a steel tube. The reaction medium is saturated with dry ice, the insoluble material formed is filtered off and the filtrate is then concentrated under vacuum. The residue is taken up in acetone, filtered off and dried to give 5.25 g of the expected acid, which is identified by its IR and NMR spectra. The product melts at 350° C. with decomposition.

C) Ethyl ester of (R,S)-2-amino-2-cyclohexylpropionic acid 3 g of the acid prepared in the previous step are added to 40 ml of absolute alcohol saturated with gaseous hydrogen chloride and the mixture is then refluxed for 20 hours, with stirring. The reaction medium is evaporated under vacuum and the residue is taken up in an ether/water mixture, which is brought to pH 9 by adding a saturated solution of sodium bicarbonate. The organic phase is decanted, washed with a saturated solution of sodium chloride and the evaporated under vacuum to give 2.1 g of the expected ester in the form of an oil. Identification by IR and NMR spectra.

D) Ethyl valerimidate

This compound is prepared in the form of the hydrochloride according to Mac Elvain (J. Amer. Chem. Soc., 1942, 64, 1825-1827). It is freed from its hydrochloride by reaction with potassium carbonate and is then extracted with DCM.

E) (R,S)-2-n-Butyl-4-cyclohexyl-4-methyl-2-imidazolin-5-one 2 g of the ester prepared in step C) and 2.35 g of ethyl valerimidate are mixed in 6 ml of xylene, to which 6 drops of acetic acid are added; the mixture is refluxed for 6 hours. The reaction medium is then concentrated under vacuum and the residue is chromatographed on fine silica gel using a chloroform/methanol/acetic acid mixture (95/9/3; v/v/v) as the eluent. The fractions containing the desired product are combined and then evaporated under vacuum; the residue is taken up with an ethyl acetate/water mixture and the pH is brought to 9 by adding a solution of sodium hydroxide. The organic phase is decanted, washed with water and then a saturated solution of sodium chloride, dried over sodium sulfate and then evaporated to dryness to give the expected product in the form of a thick oil, which solidifies to give an amorphous solid.

m = 1.56 mg.

IR (chloroform): 1720 cm$^{-1}$: C=O; 1640 cm$^{-1}$: C=N.

NMR consistent.

F) Ethyl (R,S)-4-(2-n-butyl-4-cyclohexyl-4-methyl-5-oxo-2-imidazolin-1-yl)methylbiphenyl-2-(N-methoxycarbonyl)carboximidate

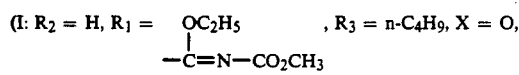

(I: $R_2 = H$, $R_1 = $ —C(OC$_2$H$_5$)=N—CO$_2$CH$_3$, $R_3 = $ n-C$_4$H$_9$, X = O, $R_4 = $ methyl, $R_5 = $ cyclohexyl)

270 mg of an 80% suspension of sodium hydride in oil are suspended in 10 ml of anhydrous DMF under argon and 1.9 g of the compound prepared in step E) are added in small portions at 0° C. After stirring for 20 minutes at RT under argon, 5 g of the compound prepared in Examples 1-2, step C), dissolved in 15 ml of anhydrous DMF, are added. After stirring for 1 hour at RT under argon, the DMF is concentrated under vacuum and the oil obtained is taken up in 100 ml of ethyl acetate. The mixture is washed with 50 ml of water, 50 ml of a 5% solution of potassium hydrogensulfate and then a saturated solution of sodium chloride and 50 ml of a saturated solution of sodium hydrogencarbonate. The organic phase is dried, filtered and concentrated. The residual oil is chromatographed on silica using a heptane/AcOEt mixture (8/2; v/v) as the eluent to give the expected product.

m = 3.10 g.

Mass spectrum: MH$^+$ = 532.

NMR spectrum: 0.9 ppm: t:3H:CH$_3$ (nBu); 1.0 ppm: t:3H:OCH$_2$-CH$_3$; 1.0-1.9 ppm: m:18H:4-cyclohexyl, 4—CH$_3$, CH$_2$—CH$_2$—CH$_2$—CH$_3$ (nBu); 2.4 ppm: t:2H:CH$_2$—CH$_2$—CH$_2$—CH$_3$(nBu); 3.4 ppm: s:2H:CO$_2$—CH$_3$; 3.55 ppm: t:2H:OCH$_2$—CH$_3$; 4.7 ppm: s:2H:CH$_2$—C$_6$H$_4$—; 7.2-7.6 ppm: m:8H:aromatic.

G) (R,S)-2-n-Butyl-4-cyclohexyl-4-methyl-1-[(2'-(5-oxo-1,2,4-oxadiazol-3-yl)biphenyl-4-yl)methyl]-2-imidazolin-5-one 354 mg of 95% sodium methylate in methanol and 432 mg of hydroxylamine hydrochloride in 25 ml of methanol are placed in a round-bottomed flask under argon. The mixture is stirred for 15 minutes at RT and 3 g of the compound obtained in the previous step in 25 ml of methanol are then added. The reaction medium is refluxed under argon for 15 hours, with constant vigorous stirring. It is concentrated, taken up with 50 ml of DCM and then extracted with 50 ml of hydrochloric acid (pH 5) and then 50 ml of a solution of sodium hydroxide (pH 13). The alkaline phase is acidified to pH 2 and extracted with twice 50 ml of DCM and the organic phase is then dried over sodium sulfate and concentrated. The residue is chromatographed on silica using a heptane/AcOEt/AcOH mixture (80/20/1.5) as the eluent. The expected product is obtained in the form of an oil, which crystallizes after trituration in an ether/hexane mixture.

m = 1 g.

M.p. = 210°-215° C.

Mass spectrum: MH$^+$: 487.

NMR spectrum: 0.7 ppm: t: 3H: CH$_3$ (nBu) 0.8-1.8 ppm: m: 18H: 4-cyclohexyl, 4-methyl, CH$_2$—CH$_2$—CH$_2$—CH$_3$ (nBu); 2.25 ppm: t: 2H: CH$_3$—CH$_2$—CH$_2$—CH$_2$—(nBu); 4.6 ppm: s: 2H: CH$_2$—C$_6$H$_4$—; 7.1-7.6 ppm: m: 8H: aromatic; 12.3 ppm: s: 1H: NH.

EXAMPLE 13

2-n-Butyl-4-cyclohexyl-4-methyl-1-[(2'-(5-oxo-1,2,4-oxadiazol-3-yl)biphenyl-4-yl)methyl]-2-imidazolin-5-one, dextrorotatory A) 5-Methyl-5-phenylhydantoin 30 g of acetophenone, diluted in 250 ml of 95° alcohol, are added over 30 minutes to a mixture of 18.35 g of sodium cyanide and 125 g of ammonium carbonate in 250 ml of water and the reaction medium is heated at 60°-65° C. for 22 hours, with stirring. It is concentrated to half its volume under vacuum and the solid which has precipitated is filtered off, washed with water and ether and then dried under vacuum to give 38 g of a white solid, which is identified by IR.

M.p. = 190°-192° C.

B) (R,S)-2-Aminophenylpropionic acid 20 g of the compound prepared in the previous step are added to a mixture of 75 g of barium hydroxide octahydrate in 500 ml of water and the reaction medium is then heated at 160° C. for 5 hours in a steel tube. It is saturated with dry ice and the precipitate is then filtered off. The filtrate is concentrated under vacuum and the white solid formed is taken up in acetone, filtered off, washed with acetone and ether and then dried to give 15.3 g of the expected acid.

M.p. = 260°-265° C. (with decomposition).

C) Ethyl ester of (R,S)-2-amino-2-phenylpropionic acid 24 g of the acid prepared in the previous step are added with a spatula to a solution of 80 g of gaseous hydrogen chloride in 210 ml of absolute ethanol, with stirring, and the mixture is refluxed for 6 and a half hours. It is concentrated under vacuum, the residue is taken up in 600 ml of ethyl acetate and 100 ml of water, and 2N sodium hydroxide is added to pH 9. The organic phase is decanted, washed with water and a saturated solution of sodium chloride, dried over sodium sulfate and then concentrated under vacuum to give 25.5 g of the expected product in the form of an oil. Identification by IR.

D) Dextrorotatory ethyl ester of 2-amino-2-phenylpropionic acid

The enantiomers of the ester prepared in the previous step are separated in accordance with the method described by Y. Sugi and S. Mitsui in Bull. Chem. Soc. Japan, 1969, 42, 2984-2988. 19.8 g of L(+)-tartaric acid are added to the 25.5 g of ester obtained in step C), diluted in 210 ml of absolute ethanol. The mixture is heated to 60° C. to give a total solution and is then left at RT for 4 hours. The crystals formed are filtered off, then rinsed with twice 70 ml of absolute alcohol, then redissolved in 200 ml of alcohol at the boil and then left at RT for 72 hours. The acicular crystals formed are filtered off, rinsed with twice 30 ml of alcohol and then dried under vacuum to give 11.9 g of the tartaric acid salt of the expected dextrorotatory ester.

M.p.=172°-173° C.

$[\alpha]_D = +44.5°$ (C=1, water).

The remaining alcohol solution is enriched in the tartaric acid salt of the levorotatory ester.

6.1 g of the tartaric acid salt of the dextrorotatory ester are taken up in 30 ml of water and then 200 ml of ethyl acetate, and 5N sodium hydroxide is added to pH 9. The organic phase is decanted, washed with water and a saturated solution of sodium chloride, dried over sodium sulfate and then concentrated under vacuum to give 3.33 g of the expected product in the form of an oil.

$[\alpha]_D = +24°$ (C=2, ethanol).

Identification by NMR.

E) Levorotatory ethyl ester of 2-amino-2-phenylpropionic acid

The alcohol solution obtained in the previous step is concentrated under vacuum after separation of the crystals of the tartaric acid salt of the dextrorotatory ethyl ester of 2-amino-2-phenylpropionic acid. The solid residue is taken up in 150 ml of water and 600 ml of ethyl acetate and the pH is brought to 9 by adding 5N sodium hydroxide. The organic phase is decanted, washed with water and a saturated solution of sodium chloride, dried over sodium sulfate and then concentrated under vacuum to give 20.6 g of the ester enriched in the levorotatory isomer.

15.9 g of D(−)-tartaric acid are added to 20.5 g of this ester, diluted in 200 ml of absolute ethanol, and dissolved at the boiling point of the alcohol. After 5 hours at RT, the acicular crystals formed are filtered off, washed with twice 50 ml of absolute alcohol and then dried under vacuum to give 16.3 g of the tartaric acid salt of the expected product.

M.p.=172°-173° C.

$[\alpha]_D = -45.2°$ (C=1, water).

6 g of the salt obtained are taken up in 50 ml of water and 200 ml of ethyl acetate and the pH is brought to 9.5 by adding 5N sodium hydroxide. The organic phase is decanted, washed with water and a saturated solution of sodium chloride and then dried over sodium sulfate and concentrated under vacuum to give 3.31 g of the expected product in the form of an oil, which is identifiable by NMR.

$[\alpha]_D = -25.5°$ (C=1, ethanol).

F) Levorotatory ethyl ester of 2-amino-2-cyclohexylpropionic acid 3.30 g of the levorotatory ester obtained in the previous step are diluted in 120 ml of acetic acid; 1.5 g of platinum oxide are added and hydrogenation is then carried out at atmospheric pressure. After 40 hours of hydrogenation, the reaction medium is filtered and then concentrated under vacuum. The residue is taken up in an ether/water mixture, and 6N hydrochloric acid is added to pH 2. The aqueous phase is decanted and ethyl acetate is then added, followed by 5N sodium hydroxide to pH 9.5. The organic phase is decanted, washed with water and a saturated solution of sodium chloride, dried over sodium sulfate and then concentrated under vacuum to give 3.20 g of the expected product.

$[\alpha]_D = -19.2°$ (C=1, ethanol). Literature: W. A. Bonner et al., J. Amer. Chem. Soc., 1956, 78, 3218-3221.

Identification by NMR.

G) 2-n-Butyl-4-cyclohexyl-4-methyl-2-imidazolin-5-one, dextrorotatory

A mixture containing 3 g of the levorotatory ester obtained in the previous step, 4.7 g of ethyl valerimidate and 8 drops of acetic acid in 15 ml of xylene is brought to the reflux point, with stirring.

After 7 hours of reflux, the reaction medium is concentrated under vacuum. The residue is chromatographed on silica using a chloroform/methanol/acetic acid mixture (95/9/3) as the eluent. The fractions containing the product are combined and concentrated under vacuum. The residue is taken up in an ethyl acetate/water mixture and the pH is brought to 9 by adding 5N sodium hydroxide. The organic phase is decanted, washed with water and a saturated solution of sodium chloride, dried over sodium sulfate and concentrated under vacuum to give an oil, which becomes an amorphous solid.

m=2.36 g.

$[\alpha]_D = +56.9°$ (C=1, chloroform).

IR (chloroform): 1720 cm$^{-1}$: C=O; 1640 cm$^{-1}$: C=N.

The IR spectrum confirms the 5-one form of the imidazolinone in solution.

H) 2-n-Butyl-4-cyclohexyl-4-methyl-1-[(2'-(5-oxo-1,2,4-oxadiazol-3-yl)biphenyl-4-yl)methyl]-2-imidazolin-5-one, dextrorotatory The subsequent procedure is as in Example 12, steps F) and G), and the expected product is obtained.

$[\alpha]_D = +30.1°$ (C=1, methanol).

The NMR spectrum is superimposable on that of Example 12.

EXAMPLE 14

(R,S)-2-n-Butyl-4-cyclohexyl-4-methyl-1-[(2'-(3-oxo-1,2,4-triazol-5-yl)biphenyl-4-yl)methyl]-2-imidazolin-5-one

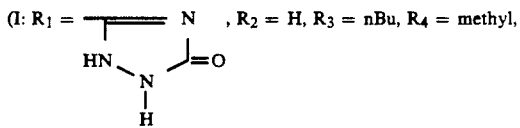

(I: $R_1 =$ , $R_2 =$ H, $R_3 =$ nBu, $R_4 =$ methyl, $R_5 =$ cyclohexyl, X = O)

40 mg of hydrazine hydrochloride are dissolved in 5 ml of anhydrous methanol under nitrogen, 30 mg of sodium methylate are then added slowly in the cold and the mixture is stirred at RT for 20 minutes under nitrogen. 290 mg of the compound prepared in Example 12, step F), dissolved in 10 ml of anhydrous methanol, are added and the reaction medium is refluxed under nitrogen for 24 hours. It is purified by chromatography on silica using a heptane/acetone mixture (8/2; v/v) as the eluent.

m=160 mg.

M.p.=256°-260° C.

Mass spectrum: MH+: 486.

NMR spectrum: 0.8 ppm: t: 3H: CH$_3$ (nBu); 0.9-1.8 ppm: m: 18H: 4-cyclohexyl, 4-methyl, CH$_2$—CH$_2$—CH$_2$—CH$_3$ (nBu); 2.25 ppm: t: 2H: CH$_2$—CH$_2$—CH$_2$—CH$_3$; 7.7 ppm: s: 2H: CH$_2$—C$_6$H$_4$—; 7.1-7.6 ppm: m: 8H: aromatic; 11 ppm: d: 2H: 2 NH;

EXAMPLE 15

2-n-Butyl-4-spirocyclopentane-1-[(2'-(3-ethoxycarbonyl-1-hydroxyureido)biphenyl-4-yl)methyl]-2-imidazolin-5-one

(I: $R_1 = $ —N(OH)—CONH—COOC$_2$H$_5$, $R_2 = $ H, $R_3 = $ n-C$_4$H$_9$, CR$_4$R$_5 = $ cyclopentane, X = O)

A) 4-Methyl-2'-nitrobiphenyl 11.2 g of 2-nitrobromobenzene are mixed with 15 g of 4-iodotoluene and the mixture is heated to 195° C. and stirred at this temperature for 3 and a half hours. After returning to RT, it is taken up with DCM and heated to the reflux point, the hot solution is filtered on Célite ® and the DCM is then evaporated off.

m=6.5 g.

The product is purified by distillation and the fraction which distils at between 80° and 120° C. under 0.2 mm Hg is recovered.

B) 4-Bromomethyl-2'-nitrobiphenyl

A mixture containing 6.5 g of 4-methyl-2'-nitrobiphenyl and 5.42 g of NBS in 50 ml of carbon tetrachloride is refluxed for 5 hours. It is cooled to 0° C. and filtered and the filtrate is concentrated to give 9 g of an oily product, which is used as such in the next step.

C) 2-n-Butyl-1-[(2'-nitrobiphenyl-4-yl)methyl]-4-spirocyclopentane-2-imidazolin-5-one A mixture containing 260 mg of an 80% suspension of sodium hydride in 5 ml of DMF is prepared and 500 mg of 2-n-butyl-4-spirocyclopentane-2-imidazolin-5-one are added at RT under nitrogen. After stirring for 15 minutes, 901 mg of 4-bromomethyl-2'-nitrobiphenyl in 5 ml of DMF are added and stirring is continued for 24 hours. The reaction medium is concentrated to dryness and taken up with a water/ethyl acetate mixture. The organic phase is decanted, dried over sodium sulfate and filtered and the ethyl acetate is then evaporated off. The product obtained is chromatographed on silica using a DCM/ethyl acetate mixture (9/1; v/v) as the eluent to give 500 mg of the expected product.

D) 2-n-Butyl-4-spirocyclopentane-1-[(2'-(3-ethoxycarbonyl-1-hydroxyureido)biphenyl-4-yl)methyl]-2-imidazolin-5-one 2 g of the compound prepared in the previous step and 310 mg of ammonium chloride are partially dissolved in 100 ml of dioxane and 100 ml of water. 654 mg of zinc powder are added under argon, with vigorous stirring. The reaction medium is heated at 65° C. for 45 minutes, with stirring. The zinc oxide formed is filtered off on Célite ®. It is rinsed with a warm dioxane/water mixture and then with warm DCM. The filtrate is cooled in ice and extracted with 20 ml of DCM. The organic phase is washed with 10 ml of water and then dried over sodium sulfate and concentrated under vacuum. The residue is taken up with 20 ml of DCM, 0.52 ml of ethoxycarbonyl isocyanate, diluted in 10 ml of DCM, is added and the mixture is stirred at RT for 30 minutes. It is concentrated to dryness, the oil obtained is then triturated in an ether/hexane mixture and the precipitate formed is filtered off.

m=800 mg.

Mass spectrum: MH+: 507.

NMR spectrum: 0.85 ppm: t: 3H: CH$_3$ (nBu); 1.2–1.4 ppm: m: 5H: CH$_3$—CH$_2$O—, CH$_3$—CH$_2$—CH$_2$—CH$_2$—; 1.55 ppm: quint: 2H: CH$_3$—CH$_2$—CH$_2$—CH$_2$—; 1.6–2 ppm: m: 8H: cyclopentane; 2.4 ppm: t: 2H: CH$_3$—CH$_2$—CH$_2$—CH$_2$—; 4.1 ppm: q: 2H: CH$_3$—CH$_2$—O; 4.8 ppm: s: 2H: CH$_2$—C$_6$H$_4$—; 7.2–7.6 ppm: m: 8H: aromatic; 9.3 ppm: s: 1H: N—OH; 10.65 ppm: s: 1H: NH—CO.

EXAMPLE 16

2-n-Butyl-1-[(2'-(3,5-dioxo-1,2,4-oxadiazol-2-yl)biphenyl-4-yl)methyl]-4-spirocyclopentane-2-imidazolin-5-one

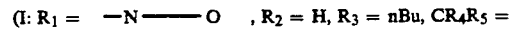
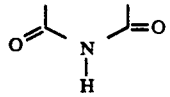

(I: $R_1 = $ <image inline>, $R_2 = $ H, $R_3 = $ nBu, CR$_4$R$_5 = $ cyclopentane, X = O)

316 μl of triton B at a concentration of 40% in methanol are placed in a 500 ml round-bottomed flask. 800 mg of the compound prepared in the previous Example, dissolved in 20 ml of hot anhydrous methanol, are added. The mixture is refluxed at 70° C. for 1 hour, left to cool and then concentrated to dryness. 1.5 ml of normal hydrochloric acid are added to the reaction medium, which is diluted with 10 ml of water. The mixture is extracted with 3 times 10 ml of DCM and the organic phases are then combined, washed with 10 ml of water, dried over sodium sulfate and concentrated. The aqueous phase is brought to pH 6–7 by adding a saturated solution of sodium hydrogencarbonate and is extracted with 3 times 10 ml of DCM. The organic phases are combined, washed with water, dried and concentrated with the first organic phase obtained. The crude product obtained is chromatographed using a DCM/methanol mixture (100/4; v/v) as the eluent. The resulting product is triturated in an ether/hexane mixture and the precipitate formed is filtered off to give 135 mg of the expected product.

M.p.=143° C.

Mass spectrum: MH+: 461.

NMR spectrum: 0.7 ppm: t: 3H: CH$_3$ (nBu); 1.2 ppm: sext: 2H: CH$_3$—CH$_2$—CH$_2$—CH$_2$—; 1.4 ppm: quint: 2H: CH$_3$—CH$_2$—CH$_2$—CH$_2$—; 1.6–1.9 ppm: m: 8H: cyclopentane; 2.5 ppm: t: 2H: CH$_2$—C$_6$H$_4$—; 7.15–7.8 ppm: m: 8H: aromatic.

EXAMPLE 17

2-n-Butyl-1-[(2'-ethylimidobiphenyl-4-yl)methyl]-4-spirocyclopentane-2-imidazolin-5-one

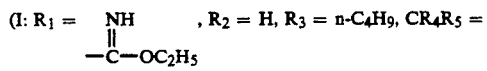

(I: $R_1 = $ —C(=NH)—OC$_2$H$_5$, $R_2 = $ H, $R_3 = $ n-C$_4$H$_9$, CR$_4$R$_5 = $ cyclopentane, X = O)

This compound is prepared from that obtained in Example 11, step A). 1 g of this product is dissolved in 10 ml of DCM, and 55 ml of a molar solution of triethyl ether tetrafluoroborate (Et$_3$O+BF$_4$−) in DCM are added under argon. The mixture is stirred under argon at RT for 24 hours. 15 ml of water are added to the reaction medium, which is then left to decant. The aqueous phase is extracted with DCM. The organic phase is washed with a dilute solution of sodium hydrogencarbonate. The organic phases are combined, dried over sodium sulfate and concentrated. The crude product obtained is chromatographed on silica using ethyl acetate as the eluent.

m = 340 mg.
M.p. = 86° C.
NMR spectrum: 0.9 ppm: m: 6H: $CH_3$ (nBu), $CH_3$ (Et); 1.3 ppm: sext: 2H: $CH_3$—$CH_2$—$CH_2$—$CH_2$—; 1.55 ppm: quint: 2H: $CH_3$—$CH_2$—$CH_2$—$CH_2$—; 1.6-2 ppm: m: 8H: cyclopentane; 2.4 ppm: t: 2H: $CH_3$—$CH_2$—$CH_2$—$CH_2$—; 3.9 ppm: q: 2H: $CH_2$ (Et); 4.75 ppm: s: 2H: $CH_2$—$C_6H_4$—; 7.2-7.6 ppm: m: 8H: aromatic; 8.4 ppm: s: 1H: C=NH.

EXAMPLE 18

2-n-Butyl-1-[(2'-(2-oxo-1,3,4-oxadiazol-5-yl)biphenyl-4-yl)methyl]-4-spirocyclopentane-2-imidazolin-5-one

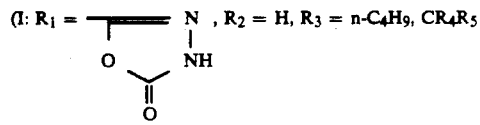

cyclopentane, X = O)

A) 4-Methylbiphenyl-2'-hydrazide 5 g of 4-methylbiphenyl-2'-carboxylic acid are dissolved in 25 ml of DCM. The reaction medium is cooled with an ice/water bath. 2.5 ml of oxalyl chloride are added dropwise and the mixture is stirred for 3 hours at RT. It is evaporated, taken up with benzene and evaporated again. 3.5 ml of hydrazine hydrate and 20 ml of THF are placed in a round-bottomed flask. The mixture is cooled with an ice/water bath and the acid chloride prepared above, dissolved in 20 ml of THF, is added dropwise. After stirring for 18 hours at RT, the reaction medium is evaporated and taken up with a water/ethyl acetate mixture and the precipitate is filtered off. The organic phase is washed with water, a 10% solution of sodium carbonate and water and then dried and evaporated. The residue obtained is chromatographed on silica using an ethyl acetate/methanol mixture as the eluent to give 1.5 g of the expected product.

B) 4-Methyl-2'-(2-oxo-1,3,4-oxadiazol-5-yl)biphenyl 6.5 g of phosgene are dissolved in 60 ml of chloroform. 1.45 g of the hydrazide prepared in step A in 40 ml of chloroform are added dropwise and the mixture is refluxed for 4 hours. It is evaporated and the residue is taken up with DCM, washed with water, dried over sodium sulfate, filtered and evaporated to give 1.48 g of the expected product.
M.p. = 123°-125° C.

C) 4-Methyl-2'-(2-oxo-3-trityl-1,3,4-oxadiazol-5-yl)biphenyl 2.03 g of the compound prepared in step B, 2.5 g of trityl chloride, 50 ml of DCM and 1.6 ml of triethylamine are placed in a round-bottomed flask and the mixture is refluxed for 1 and a half hours. It is evaporated, the residue is taken up with an ethyl ether/water mixture and the organic phase is washed with a 3% solution of potassium hydrogensulfate, dried over sodium sulfate, filtered and evaporated. The product is used in the crude form for the next step.

D) 4-Bromomethyl-2'-(2-oxo-3-trityl-1,3,4-oxadiazol-5-yl)biphenyl

The product prepared in the previous step (m = 4.5 g) is dissolved in 80 ml of carbon tetrachloride. 1.75 g of NBS and 100 mg of benzoyl peroxide are added and the mixture is refluxed for 3 hours. After returning to RT, it is filtered and the filtrate is evaporated. The crude product obtained (5.35 g) is used as such in the next step.

E) 2-n-Butyl-1-[(2'-(2-oxo-3-trityl-1,3,4-oxadiazol-5-yl)biphenyl-4-yl)methyl]-4-spirocyclopentane-2-imidazolin-5-one 400 mg of sodium hydride (as an 80% suspension in oil) and 20 ml of DMF are placed in a three-necked flask under argon. 922 mg of the 2-n-butyl-4-spirocyclopentane-2-imidazolin-5-one hydrochloride prepared in Example 1, step A, are added in portions. After stirring for 30 minutes at RT, 2.7 g of the compound prepared in step D, dissolved in 20 ml of DMF, are added and the mixture is stirred for 1 hour at RT. It is evaporated and the residue is taken up with a water/ethyl acetate mixture, dried over sodium sulfate, filtered and evaporated. The residue is chromatographed on silica using a DCM/ethyl acetate mixture (95/5; v/v/) as the eluent to give 1.6 g of the expected product.

F) 2-n-Butyl-1-[(2'-(2-oxo-1,3,4-oxadiazol-5-yl)biphenyl-4-yl)methyl]-4-spirocyclopentane-2-imidazolin-5-one 1.6 g of the compound obtained in step E are dissolved in 25 ml of 98% formic acid, 0.7 ml of concentrated sulfuric acid is added and the mixture is stirred for 3 hours at RT. It is poured into a water/ice mixture and extracted with ethyl acetate. The organic phase is washed 3 times with water, a 3% solution of sodium hydrogencarbonate, water and then a saturated solution of sodium chloride. It is dried over sodium sulfate, filtered and evaporated. The residue is chromatographed on silica using a DCM/ethyl acetate mixture (7/3; v/v) as the eluent to give 720 mg of the expected product.
M.p. = 171°-172° C.

What is claimed is:

1. A compound of the formula

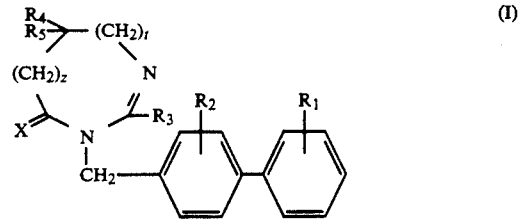

in which:
$R_1$ and $R_2$ are similar or different and are each independently hydrogen or a group selected from:
$CO_2N$=$C(NH_2)_2$,
$CONHNHCONH_2$,
$CONHNHCSNH_2$,
$C(OC_2H_5)$=$NCO_2CH_3$,
$COCH_2CO_2C_2H_5$,
$N(OH)$—$CONHCOOC_2H_5$,
$C(OC_2H_5)$=$NH$
or a nitrogen heterocycle selected from:

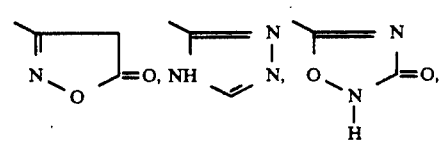

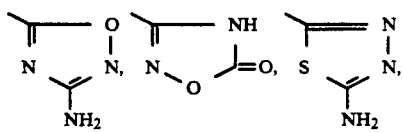 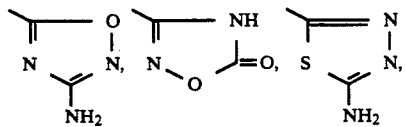

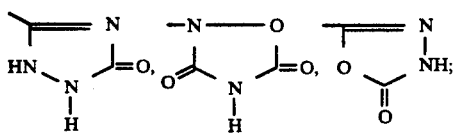 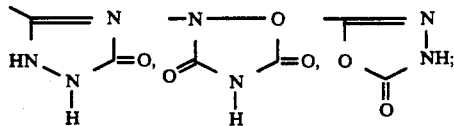

with the proviso that at least one of the substituents $R_1$ or $R_2$ is other than hydrogen;

$R_3$ is a hydrogen, a $C_1$-$C_6$ alkyl which is unsubstituted or substituted by one or more halogen atoms, a $C_2$-$C_6$ alkenyl, a $C_3$-$C_7$ cycloalkyl, a phenyl, a phenylalkyl in which the alkyl is $C_1$-$C_3$ or a phenylalkenyl in which the alkenyl is $C_2$-$C_3$, said phenyl groups being unsubstituted or monosubstituted or polysubstituted by a halogen atom, a $C_1$-$C_4$ alkyl, a $C_1$-$C_4$ halogenoalkyl, a $C_1$-$C_4$ polyhalogenoalkyl, a hydroxyl or a $C_1$-$C_4$ alkoxy;

$R_4$ and $R_5$ are each independently a $C_1$-$C_6$ alkyl, a $C_3$-$C_7$ cycloalkyl, a phenyl or a phenylalkyl in which the alkyl is $C_1$-$C_3$, said alkyl, phenyl or phenylalkyl groups being unsubstituted or substituted by one or more halogen atoms or by a group selected from a $C_1$-$C_4$ perfluoroalkyl, a hydroxyl and a $C_1$-$C_4$ alkoxy; or $R_4$ and $R_5$, bonded together, are either a group of the formula $(CH_2)_n$ or a group of the formula $(CH_2)_pY$—$(CH_2)_q$, in which Y is either an oxygen atom, or a sulfur atom, or a carbon atom substituted by a $C_1$-$C_4$ alkyl group, a phenyl or a phenylalkyl in which the alkyl is $C_1$-$C_3$, or a group N—$R_6$, in which $R_6$ is a hydrogen, a $C_1$-$C_4$ alkyl, a phenylalkyl in which the alkyl is $C_1$-$C_3$, a $C_1$-$C_4$ alkylcarbonyl, a $C_1$-$C_4$ halogenoalkylcarbonyl, a $C_1$-$C_4$ polyhalogenoalkylcarbonyl, a benzoyl, an α-aminoacyl or an N-protecting group selected from the group consisting of tert-butoxy carbonyl, benzyloxycarbonyl, fluoroenylmethoxy carbonyl and benzyl, or $R_4$ and $R_5$, together with the carbon atom to which they are bonded, form an indane or an adamantane;

p+q=m;

n is an integer between 2 and 11;

m is an integer between 2 and 5;

X is an oxygen atom or a sulfur atom; and z and t are simultaneously zero or one is zero and the other is 1;

and its salts.

2. A compound according to claim 1 in which:

$R_1$ is in the ortho position and is a nitrogen heterocycle selected from:

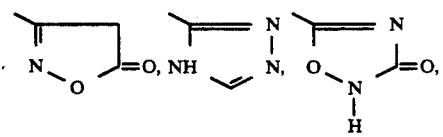

$R_2$ is hydrogen;

$R_3$ is a $C_1$-$C_6$ alkyl;

$R_4$ and $R_5$, together with the carbon to which they are attached, are a group of the formula $(CH_2)_n$;

n is equal to 4 or 5;

z and t are zero or z is 1 and t is zero; and

X is an oxygen atom;

and its salts.

3. A pharmaceutical composition comprising an effective amount of a compound according to claim 1 in admixture with a pharmaceutically acceptable excipient.

4. A compound of the formula

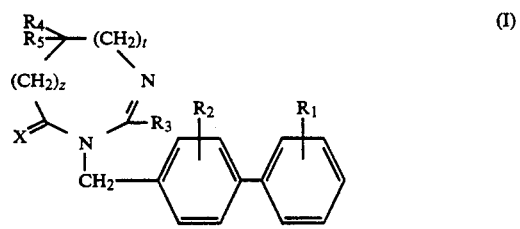

(I)

in which:

$R_1$ and $R_2$ are similar or different and are each independently hydrogen or a group selected from:
$CO_2N$=$C(NH_2)_2$,
$CONHNHCONH_2$,
$CONHNHCSNH_2$,
$C(OC_2H_5)$=$NCO_2CH_3$,
$COCH_2CO_2C_2H_5$,
$N(OH)$—$CONHCOOC_2H_5$,
$C(OC_2H_5)$=$NH$ or a nitrogen heterocycle selected from:

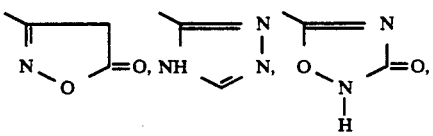

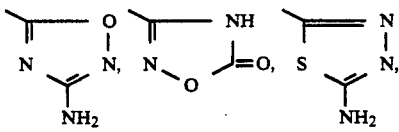

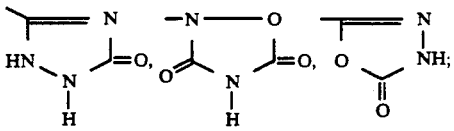

with the proviso that at least one of the substituents $R_1$ or $R_2$ is other than hydrogen;

$R_3$ is a hydrogen, a $C_1$-$C_6$ alkyl which is unsubstituted or substituted by one or more halogen atoms, a $C_2$-$C_6$ alkenyl, a $C_3$-$C_7$ cycloalkyl, a phenyl, a phenylalkyl in which the alkyl is $C_1$-$C_3$, or a phenylalkenyl in which the alkenyl is $C_2$-$C_3$, said phenyl groups being unsubstituted or monosubstituted or polysubstituted by a halogen atom, a $C_1$-$C_4$ alkyl, a $C_1$-$C_4$ halogenoalkyl, a $C_1$-$C_4$ polyhalogenoalkyl, a hydroxyl or a $C_1$-$C_4$ alkoxy;

$R_4$ and $R_5$ are each independently a $C_1$-$C_6$ alkyl, a $C_3$-$C_7$ cycloalkyl, a phenyl or a phenylalkyl in which the alkyl is $C_1$-$C_3$, said alkyl, phenyl or phenylalkyl groups being unsubstituted or substituted by one or more halogen atoms or by a group selected from a $C_1$-$C_4$ perfluoroalkyl, a hydroxyl and a $C_1$-$C_4$ alkoxy; or $R_4$ and $R_5$, bonded together, are either a group of the formula $(CH_2)_n$ or a group of the formula $(CH_2)_pY$—$(CH_2)_q$, in which Y is either an oxygen atom, or a sulfur atom, or a carbon atom substituted by a $C_1$-$C_4$ alkyl group, a phenyl or a phenylalkyl in which the alkyl is $C_1$-$C_3$, or a group N-$R_6$, in which $R_6$ is a hydrogen, a $C_1$-$C_4$ alkyl, a phenylalkyl in which the alkyl is $C_1$-$C_3$, a $C_1$-$C_4$ alkylcarbonyl, a $C_1$-$C_4$ halogenoalkylcarbonyl, a $C_1$-$C_4$ polyhalogenoalkylcarbonyl, a benzoyl, an α-aminoacyl or an N-protecting group selected from the group consisting of tert-butoxy carbonyl, benzyloxycarbonyl, fluoroenylmethoxy carbonyl and benzyl, or $R_4$ and $R_5$, together with the carbon atom to which they are bonded, form an indane or an adamantane;

$p+q=m$;

n is an integer between 2 and 11;

m is an integer between 2 and 5;

X is an oxygen atom or a sulfur atom; and z and t are zero;

and its salts.

5. A compound of the formula

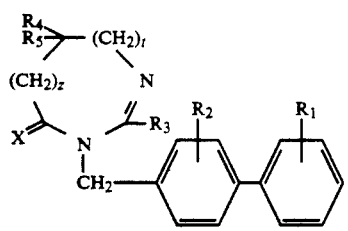

in which:

$R_1$ and $R_2$ are similar or different and are each independently hydrogen or a group selected from:
$CO_2N=C(NH_2)_2$,
$CONHNHCONH_2$,
$CONHNHCSNH_2$,
$C(OC_2H_5)=NCO_2CH_3$,
$COCH_2CO_2C_2H_5$,
$N(OH)$—$CONHCOOC_2H_5$,
$C(OC_2H_5)=NH$ or a nitrogen heterocycle selected from:

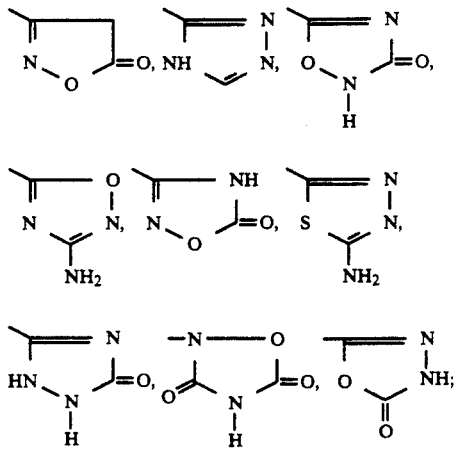

with the proviso that at least one of the substituents $R_1$ or $R_2$ is other than hydrogen;

$R_3$ is a hydrogen, a $C_1$-$C_6$ alkyl which is unsubstituted or substituted by one or more halogen atoms, a $C_2$-$C_6$ alkenyl, a $C_3$-$C_7$ cycloalkyl, a phenyl, a phenylalkyl in which the alkyl is $C_1$-$C_3$, or a phenylalkenyl in which the alkenyl is $C_2$-$C_3$, said phenyl groups being unsubstituted or monosubstituted or polysubstituted by a halogen atom, a $C_1$-$C_4$ alkyl, a $C_1$-$C_4$ halogenoalkyl, a $C_1$-$C_4$ polyhalogenoalkyl, a hydroxyl or a $C_1$-$C_4$ alkoxy;

$R_4$ and $R_5$ are each independently a $C_1$-$C_6$ alkyl, a $C_3$-$C_7$ cycloalkyl, a phenyl or a phenylalkyl in which the alkyl is $C_1$-$C_3$, said alkyl, phenyl or phenylalkyl groups being unsubstituted or substituted by one or more halogen atoms or by a group selected from a $C_1$-$C_4$ perfluoroalkyl, a hydroxyl and a $C_1$-$C_4$ alkoxy; or $R_4$ and $R_5$, bonded together, are either a group of the formula $(CH_2)_n$ or a group of the formula $(CH_2)_pY$—$(CH_2)_q$, in which Y is either an oxygen atom, or a sulfur atom, or a carbon atom substituted by a $C_1$-$C_4$ alkyl group, a phenyl or a phenylalkyl in which the alkyl is $C_1$-$C_3$, or a group N—$R_6$, in which $R_6$ is a hydrogen, a $C_1$-$C_4$ alkyl, a phenylalkyl in which the alkyl is $C_1$-$C_3$, a $C_1$-$C_4$ alkylcarbonyl, a $C_1$-$C_4$ halogenoalkylcarbonyl, a $C_1$-$C_4$ polyhalogenoalkylcarbonyl, a benzoyl, an α-aminoacyl or an N-protecting group selected from the group consisting of tert-butoxy carbonyl, benzyloxycarbonyl, fluoroenylmethoxy carbonyl and benzyl, or $R_4$ and $R_5$, together with the carbon atom to which they are bonded, form an indane or an adamantane;

$p+q=m$;

n is an integer between 2 and 11;

m is an integer between 2 and 5;

X is an oxygen atom or a sulfur atom; and z is zero;

t is 1;

and its salts.

* * * * *